(12) United States Patent
Calabotta et al.

(10) Patent No.: US 9,999,648 B2
(45) Date of Patent: Jun. 19, 2018

(54) COMBINATION AND/OR COMPOSITION COMPRISING BACILLUS, AND YUCCA, QUILLAJA, OR BOTH AND A METHOD FOR USING AND MAKING

(71) Applicants: Phibro Animal Health Corporation, Teaneck, NJ (US); Desert King International, LLC, San Diego, CA (US)

(72) Inventors: David Calabotta, Quincy, IL (US); Wendell Knehans, St. Louis, MO (US); Derek McLean, Corvallis, OR (US)

(73) Assignees: Phibro Animal Health Corporation, Teaneck, NJ (US); Desert King International, LLC, San Diego, CA (US)

( * ) Notice: Subject to any disclaimer, the term of this patent is extended or adjusted under 35 U.S.C. 154(b) by 0 days. days.

(21) Appl. No.: 14/699,740

(22) Filed: Apr. 29, 2015

(65) Prior Publication Data

US 2015/0250842 A1    Sep. 10, 2015

Related U.S. Application Data

(63) Continuation of application No. PCT/US2014/062283, filed on Oct. 24, 2014.

(60) Provisional application No. 61/895,980, filed on Oct. 25, 2013.

(51) Int. Cl.
| | |
|---|---|
| *A61K 36/38* | (2006.01) |
| *A23K 1/00* | (2006.01) |
| *A23K 1/16* | (2006.01) |
| *A61K 36/185* | (2006.01) |
| *A61K 36/88* | (2006.01) |
| *A61K 35/742* | (2015.01) |
| *A23K 10/18* | (2016.01) |
| *A23K 10/30* | (2016.01) |
| *A23K 20/00* | (2016.01) |
| *A23K 20/10* | (2016.01) |
| *A23K 50/10* | (2016.01) |
| *A23K 50/75* | (2016.01) |
| *A23K 50/30* | (2016.01) |
| *A23K 50/40* | (2016.01) |
| *A23K 50/80* | (2016.01) |
| *A23L 33/105* | (2016.01) |
| *A23L 33/135* | (2016.01) |
| *A61K 35/00* | (2006.01) |

(52) U.S. Cl.
CPC .............. *A61K 36/88* (2013.01); *A23K 10/18* (2016.05); *A23K 10/30* (2016.05); *A23K 20/00* (2016.05); *A23K 20/10* (2016.05); *A23K 50/10* (2016.05); *A23K 50/30* (2016.05); *A23K 50/40* (2016.05); *A23K 50/75* (2016.05); *A23K 50/80* (2016.05); *A23L 33/105* (2016.08); *A23L 33/135* (2016.08); *A61K 35/742* (2013.01); *A61K 36/185* (2013.01); *A61K 2035/115* (2013.01)

(58) Field of Classification Search
CPC .................. A61K 35/742; A61K 36/88; A61K 2035/115; A23L 33/135; A23K 10/18
See application file for complete search history.

(56) References Cited

U.S. PATENT DOCUMENTS

| | | | |
|---|---|---|---|
| 6,485,734 B1 | 11/2002 | Baker et al. | |
| 2011/0256216 A1* | 10/2011 | Lefkowitz | A23D 9/007 424/451 |

FOREIGN PATENT DOCUMENTS

| | | |
|---|---|---|
| CN | 103289910 | 9/2013 |
| JP | 07-107923 | 4/1995 |
| JP | 08-099884 | 4/1996 |
| JP | 08-131089 | 5/1996 |
| JP | 2002-370993 | 12/2002 |
| JP | 2006-061092 A | 3/2006 |
| KR | 2012-0069221 | 6/2012 |
| WO | WO 93/14187 | 7/1993 |
| WO | WO 94/11492 | 5/1994 |
| WO | WO 2005092122 A1 * | 6/2005 |
| WO | WO 2015/155293 | 10/2015 |

OTHER PUBLICATIONS

Ashida et al., "Protection of Japanese Flounder *Paralichthys olivaceus* against Experimental Edwardsiellosis by Formalin-killed *Edwardsiella tarda* in Combination with Oral Administration of Immunostimulants," *Fisheries Science* 65(4):527-530, Aug. 1, 1999.
Francis et al., "*Quillaja* saponins—a natural growth promoter for fish,"*Animal Feed Science and Technology* 121(1-2):147-157, Jun. 9, 2005.
Kensil et al, "Saponins as vaccine adjuvants," *Critical Reviews in Therapeutic Drug Carrier Systems* 13(1/02):1-55, Jan. 1, 1996 (Abstract only).

(Continued)

*Primary Examiner* — Padmavathi Baskar
(74) *Attorney, Agent, or Firm* — Klarquist Sparkman, LLP

(57) ABSTRACT

The present disclosure concerns embodiments of a combination and/or composition comprising *bacillus*, and *yucca, quillaja* or both. Embodiments of methods of making and using the combination and/or composition also are disclosed herein. In some embodiments, the combination and/or composition may be used to improve feed conversion rates in animals. In some embodiments the animals are avians; in other embodiments, the animals are non-avians. Embodiments of the disclosed combination can comprise a first composition comprising *Quillaja saponaria*, *Yucca schidigera*, or both, and *Bacillus coagulans*. Embodiments of the disclosed composition can comprise *Quillaja saponaria*, *Yucca schidigera*, or both, and *Bacillus coagulans*.

14 Claims, 34 Drawing Sheets

(56) References Cited

OTHER PUBLICATIONS

Marais et al., "Control of Plant-Parasitic Nematodes with Bionematicides Nema-Q® An Extract of Quillaja Saponaria," *Journal of Nematology* 42(3):254-255, Sep. 1, 2010.

Olusola et al., "The potentials of medicinal plant extracts as bio-antimicrobials in aquaculture," *International Journal of Medicinal and Aromatic Plants*, 3(3):404-412, Sep. 1, 2013.

Stewart-Tull, "The Use of Adjuvants in Experimental Vaccines: IV. ISCOMS.," *Methods in Molecular Medicine* 4:153-155, 1996.

Vinay et al., "Toxicity and dose determination of quillaja saponin, aluminum hydroxide and squalene in olive flounder (*Paralichthys olivaceus*)," *Veterinary Immunology and Immunopathology* 158(1):73-85, Mar. 22, 2013.

Wang et al., "Anthelmintic activity of steroidal saponins from C.H. Wright against (Monogenea) in goldfish," *Parasitology Research* 107(6):1365-1371, Aug. 6, 2010.

Written Opinion dated May 20, 2015 from PCT Application No. PCT/EP2015/057732 (International Publication No. WO 2015/155293).

Calabotta et al., "Metabolism and Nutrition: Feed Additives II—175 Impact of a proprietary blend (PB) of *Quillaja saponaria* and *Yucca schidigera* and commercially available direct fed microbials (DFM) on performance of commercial broilers," *Poultry Science* 92(E-Suppl. 1):59-62, Jul. 24, 2013.

International Search Report dated Jan. 30, 2015 from International Application No. PCT/US2014/062283.

"Product Showcase: Direct-fed Microbe," *Poultry Times* pp. 14-15, Oct. 21, 2013.

"Stop Stool Eating Chewable Tablets for Dogs," http://www.drugs.com/vet/shop/stop-stool-eating-chewable-tablets-for-dogs.html downloaded Oct. 21, 2014.

Güroy et al., "Effect of dietary *Yucca schidigera* extract on growth, total ammonia-nitrogen excretion and haematological parameters of juvenile striped catfish *Pangasianodon hypophthalmus*," *Aquaculture Research* 45(4):647-654, Mar. 2014.

Irianto et al., "Probiotics in aquaculture," *Journal of Fish Diseases* 25:1-10, Jan. 2002.

Kelly et al., "Effects of *Yucca shidigera* Extract on Growth, Nitrogen Retention, Ammonia Excretion, and Toxicity in Channel Catfish *Ictalurus punctatus* and Hybrid Tilapia *Oreochromis mossambicus* × *O. niloticus*," *Journal of the World Aquaculture Society* 34(2):156-161, Jun. 2003.

\* cited by examiner

| Ingredient Name | ABF Str Trt 1 (PC) | ABF Str Trt 2 (NC) | ABF Gwr Trt 1 (PC) | ABF Gwr Trt 2 (NC) | ABF Fin1 Trt 1 (PC) | ABF Fin1 Trt 2 (NC) | ABF Fin 2 Trt 1 (PC) | ABF Fin 2 Trt 2 | ABF Fin 2 Trt 1 (PC) | ABF Fin 2 Trt 2 |
|---|---|---|---|---|---|---|---|---|---|---|
| Corn (8.2% CP) | 1101.91 | 1104.04 | 1195.41 | 1197.14 | 1323.96 | 1324.19 | 1439.51 | 1440.24 | 1384.16 | 1384.89 |
| Soybean Meal (47.5% CP) | 663 | 663 | 568 | 568 | 455 | 455 | 451 | 451 | 397 | 397 |
| DDGS Poet (Low Fat) | 100 | 100 | 100 | 100 | 100 | 100 | | | 100 | 100 |
| Corn Oil | 49 | 49 | 57 | 57 | 51 | 51 | 45 | 45 | 53 | 53 |
| Limestone | 26 | 26 | 25 | 25 | 23 | 23 | 21 | 21 | 22 | 22 |
| Dical Phos 18.5% | 26 | 26 | 24 | 24 | 19 | 19 | 18 | 18 | 17 | 17 |
| Salt | 6.9 | 6.9 | 7 | 7 | 7 | 7 | 7 | 7 | 6.5 | 6.5 |
| S-Carb | 4 | 4 | 2.6 | 2.6 | 2 | 2 | 2 | 2 | 2 | 2 |
| DL Methionine | 3 | 3 | | | | | | | | |
| Alimet (Liq MHA) | 3.95 | 3.95 | 6.55 | 6.55 | 5.35 | 5.35 | 5.15 | 5.15 | 5 | 5 |
| Biolys-65 | 6.4 | 6.4 | 6.25 | 6.25 | 6.9 | 6.9 | 5.55 | 5.55 | 7.45 | 7.45 |
| L-Threonine | 1.35 | 1.35 | 1.35 | 1.35 | 1.45 | 1.45 | 1.4 | 1.4 | 1.5 | 1.5 |
| FS Broiler Trace Mineral Pmx | 1.5 | 1.5 | 1.5 | 1.5 | 1.25 | 1.25 | 1.2 | 1.2 | 1.2 | 1.2 |
| Brdr/Broiler Vit Pmx | 1 | 1 | 1 | 1 | 0.85 | 0.85 | 0.75 | 0.75 | 0.75 | 0.75 |
| Vit D3 6000 Pmx | 0.5 | 0.5 | 0.4 | 0.4 | | | | | | |
| GN Aniox E Blend | 0.8 | 0.8 | | | | | | | | |
| Choline Cl 70% | 1.25 | 1.25 | 1 | 1 | 0.8 | 0.8 | 0.5 | 0.5 | 0.5 | 0.5 |
| CitriStim (MOS) | 2 | -- | 1.5 | -- | 1 | -- | 1 | -- | 1 | -- |
| Calsporin 1.2 B | 1 | -- | 0.5 | -- | 0.5 | -- | 0.5 | -- | 0.5 | -- |
| Micro-Aid (DPI) | | | 0.5 | -- | 0.5 | -- | | | | |
| Safmune (Prince) | -- | 0.6 | -- | 0.5 | -- | 0.5 | -- | 0.5 | -- | 0.5 |
| Nutrafito Plus (Prince) | -- | 0.25 | -- | 0.25 | -- | 0.25 | -- | 0.25 | -- | 0.25 |
| Ganpro (Prince)* | -- | 0.01653 | -- | 0.01653 | -- | 0.01653 | -- | 0.01653 | -- | 0.01653 |
| Rovabio Max LC | 0.44 | 0.44 | 0.44 | 0.44 | 0.44 | 1.44 | 0.44 | 0.44 | 0.44 | 0.44 |
| Ingredient Total: | 2000.00 | 2000.00 | 2000.00 | 2000.00 | 2000.00 | 2000.00 | 2000.00 | 2000.00 | 2000.00 | 2000.00 |

FIG. 23

COMBINATION AND/OR COMPOSITION COMPRISING BACILLUS, AND YUCCA, QUILLAJA, OR BOTH AND A METHOD FOR USING AND MAKING

CROSS REFERENCE TO RELATED APPLICATION

This application is a continuation of International Application No. PCT/U. S. 2014/062283, filed Oct. 24, 2014, which in turn claims the benefit of the earlier filing date of U.S. Provisional Application No. 61/895,980, filed Oct. 25, 2013. These prior applications are incorporated herein in their entirety.

FIELD

The present disclosure concerns embodiments of a combination and/or a composition comprising *bacillus*, and *yucca, quillaja* or both. Also disclosed herein are embodiments of a method of making and using the disclosed combination and/or composition.

BACKGROUND

Feed conversion rates allow farmers to estimate the amount of feed required for animals, thereby providing the ability to effectively budget costs associated with raising the animals. Feed conversion rates also can be used to reduce risks associated with raising animals, such as feed shortfalls or waste. Feed conversion rates also allow farmers to determine profit margins.

A need exists in the art for methods that allow increased feed conversion (such as by reducing the feed conversion rate) to promote animal growth (such as by increasing weight) without having to increase the amount of food provided to the animal.

SUMMARY

Disclosed herein are embodiments of a composition comprising *quillaja, yucca* or both, and a *Bacillus* species. The *yucca* may be *Yucca schidigera*; the *quillaja* may be *Quillaja saponaria*; and the *Bacillus* species may be *Bacillus coagulans*. *Bacillus coagulans*. Embodiments of the composition also may further comprise a feedstuff. In some embodiments, the composition consists essentially of *Quillaja saponaria, Yucca schidigera*, or both, and *Bacillus coagulans*, and may consist of *Quillaja saponaria, Yucca schidigera* and *Bacillus coagulans*. The *Quillaja saponaria* of the disclosed composition may be a *Quillaja saponaria* plant extract; the *Yucca schidigera* may be a *Yucca schidigera* plant extract; or both may be extracts. The *Quillaja saponaria* plant extract can comprise at least one saponin, polyphenol, antioxidant, resveratrol, or any combination thereof; the *Yucca schidigera* plant extract can comprise at least one saponin, polyphenol, antioxidant, resveratrol or any combination thereof; or both may comprise at least one saponin, polyphenol, antioxidant, resveratrol or any combination thereof.

Also disclosed herein is a combination comprising a *Bacillus* species and a first composition comprising *yucca, quillaja* or both. The *quillaja* may be *Quillaja saponaria*; the *yucca* may be *Yucca* schidigera; and the *Bacillus* may be *Bacillus coagulans*. The *Bacillus coagulans* may be a second composition comprising *Bacillus coagulans*. The first composition may consist essentially of *Quillaja saponaria, Yucca schidigera*, or both, and in certain examples, the first composition consists of both *Quillaja saponaria* and *Yucca schidigera*. The *quillaja* may be a *quillaja* plant extract, and/or the *yucca* may be a *yucca* plant extract. In some examples, the *quillaja* plant extract, the *yucca* plant extract or both comprises at least one saponin. The *Quillaja saponaria* of the disclosed combination can be a *Quillaja saponaria* plant extract, the *Yucca schidigera* can be a *Yucca schidigera* plant extract, or both. In some embodiments of the combination, the *Quillaja saponaria* plant extract comprises at least one saponin, the *Yucca schidigera* plant extract comprises at least one saponin, or both.

The first and second compositions of the combination may be admixed to form an admixed composition. This admixed composition can be administered in combination with a feedstuff, or may be further admixed with a feedstuff to form a feedstuff admixture. Particular embodiments concern a combination wherein components of the admixed composition, the feedstuff admixture, or both, are sized to facilitate admixing, facilitate administration to an animal, or both.

Particular embodiments may further comprise a vitamin, an antibiotic, a trace mineral, a bulking agent, a carrier, a vaccine, a colorant, a taste enhancer, corn, soybean meal, corn oil, limestone, salt, distillers dried grains with solubles (DDGS), dicalcium phosphate, sodium sesquicarbonate, methionine source, lysine source, L-threonine, choline, or any combination thereof. The combination and/or admixed composition may be formulated particularly for administration to an animal.

Also disclosed herein are embodiments of a method comprising administering a composition or combination as disclosed herein to an animal. The method may concern administering a combination comprising a first composition comprising *Quillaja saponaria, Yucca schidigera* or both, and a second composition comprising *Bacillus coagulans*. In some examples, the first composition consists essentially of *Quillaja saponaria, Yucca schidigera* or both, and in certain examples, the first composition consists of *Quillaja saponaria* and *Yucca schidigera*. In some embodiments, the method may include using a combination that is a composition comprising *Quillaja saponaria, Yucca schidigera*, and *Bacillus coagulans*.

The method may include administering the first and second compositions substantially simultaneously. Other embodiments concern administering the first and second compositions sequentially, in any order. The composition or combination used in the disclosed method may be admixed with a feedstuff to form an admixed feedstuff, and the admixed feedstuff administered to the animal. In some examples, the first composition may be admixed with feedstuff at from greater than 0 to 10 ounces per ton of feedstuff, or from 2-6 ounces per ton of feedstuff, and the second composition may be admixed with feedstuff at from 0.5 to 50 grams per ton of feedstuff, or from 7-8 grams per ton of feedstuff. In certain examples, the mammal is a bovine, and the second composition is administered to the mammal at from 10 to 50 grams per head per day, or at from 28-36 grams per head per day. In other examples, the mammal is a swine, and the second composition is administered to the mammal at from 2 to 10 grams per head per day.

The disclosed method may comprise administering the composition or combination to a particular animal, such as an avian. For example, the avian may be chicken, turkey, goose, duck, Cornish game hen, quail, pheasant, guineafowl, ostrich, emu, swan or pigeon. In some embodiments, the chicken is a broiler meat-type chicken. In yet other embodiments, the avian is chicken, and the combination and/or admixed composition, is administered to starter chicken, grower chicken, finisher 1 chicken and/or finisher 2 chicken.

In some embodiments, the composition or combination is administered to a non-avian animal. The non-avian animal may be a mammal, fish, reptile, amphibian, insect, crustacean or mollusk. In some examples, the animal is a feed animal, utility animal or companion animal. In certain examples, the mammal is a bovine, swine, equine, canine, feline, sheep, goat, rodent, rabbit, deer or antelope. In certain examples, the non-avian animal is a feed animal, and the combination or composition is administered from weaning or hatching until harvest. The feed animal may be bovine, swine, sheep, deer, rabbit or fish, and in some examples, the fish is a salmon, trout, tilapia, bass, sea bass, bream, carp, catfish, mullet, grouper, or amberjack.

Animals of the disclosed method may have an improved feed conversion rate relative to an animal not administered the combination or composition. An improvement in the feed conversion is represented by a lower number for the feed conversion rate. Certain embodiments of the disclosed method can result in animals having a feed conversion rate that is improved by greater than 0% up to at least 5%. In particular embodiments, the feed conversion rate is improved (i.e. lowered) by at least 0.5%.

In some embodiments, administration of the combination and/or admixed composition may also have a beneficial effect on animal health, typically, a beneficial effect on the digestive system, including the stomach and intestines. Certain embodiments have a beneficial effect on villi length. Administering the combination and/or composition may also result in a lower plasma concentration of IL-6 and IL-10 relative to an animal not administered the composition or combination.

An exemplary embodiment of the method disclosed herein concerns a method of increasing feed conversion rate in avians in a commercial feed operation, comprising administering a composition comprising (a) *Bacillus coagulans*, (b) a feedstuff, and (c) *Quillaja saponaria, Yucca schidigera*, or both, to an avian to improve (i.e. lowered) feed conversion rate by greater than 0.5% up to at least 5% relative to an animal not administered the composition. In this embodiment, the avian may be selected from chicken, turkey, goose, duck, Cornish game hen, quail, pheasant, guinea-fowl, ostrich, emu, swan or pigeon. In some embodiments, the chicken is a broiler meat-type chicken.

Embodiments of a method for making a composition are also disclosed herein. The method concerns providing a first composition comprising *Quillaja saponaria, Yucca schidigera*, or both; providing a second composition comprising *Bacillus coagulans*; and combining the first and second compositions. The method may further comprise comminuting *Quillaja saponaria, Yucca schidigera*, or both, to a size suitable for formulating the first composition. In some embodiments, the *Quillaja saponaria* is a *Quillaja saponaria* plant extract; the *Yucca schidigera* is a *Yucca schidigera* plant extract; or both the *Quillaja saponaria* and the *Yucca schidigera* are plant extracts, and the method may further comprise making a *Quillaja saponaria* plant extract by extracting *Quillaja saponaria* plant material, and/or making a *Yucca schidigera* plant extract by extracting *Yucca schidigera* plant material. In some embodiments, the *Quillaja saponaria* plant extract comprises at least one saponin; the *Yucca schidigera* plant extract comprises at least one saponin; or both the *Quillaja saponaria* and *Yucca schidigera* may be plant extracts. The method may further comprise admixing the combination and/or composition with a feedstuff to form an admixed feedstuff. Particular embodiments of the disclosed method also can comprise formulating the first and/or second compositions for mixture with the feedstuff to provide a substantially homogeneous admixed feedstuff, and may further comprise administering the admixed feedstuff to an animal.

The foregoing and other objects, features, and advantages of the invention will become more apparent from the following detailed description, which proceeds with reference to the accompanying figures.

BRIEF DESCRIPTION OF THE DRAWINGS

FIG. 23 is a table of the antibiotic free (ABF) and treatment diets used in the test.

DETAILED DESCRIPTION

Figure 1:
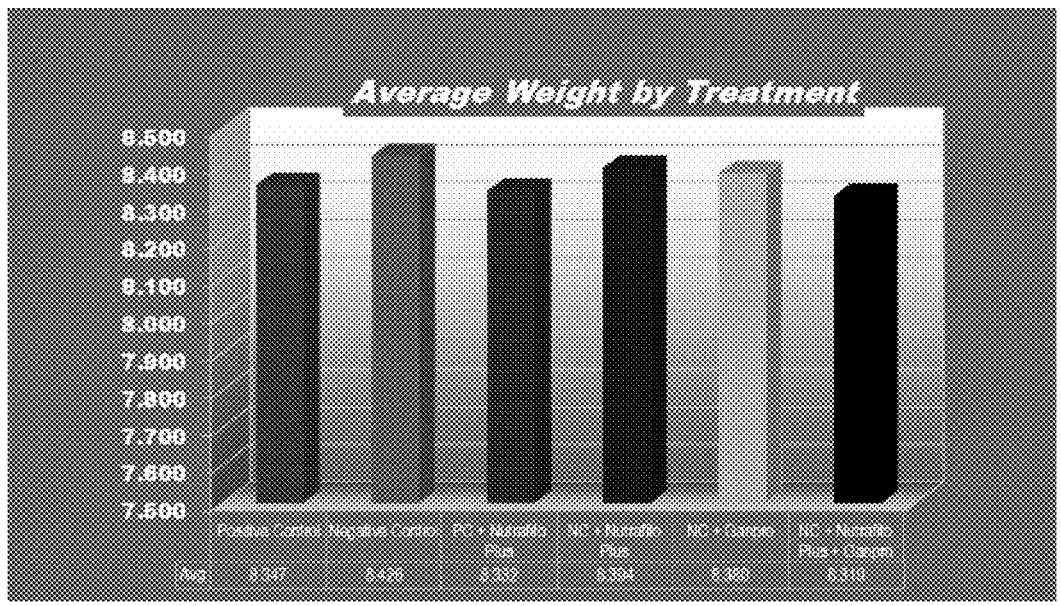
FIG. 1 is a bar graph illustrating average weight results obtained from different types of treatment embodiments disclosed herein.
Figure 2:
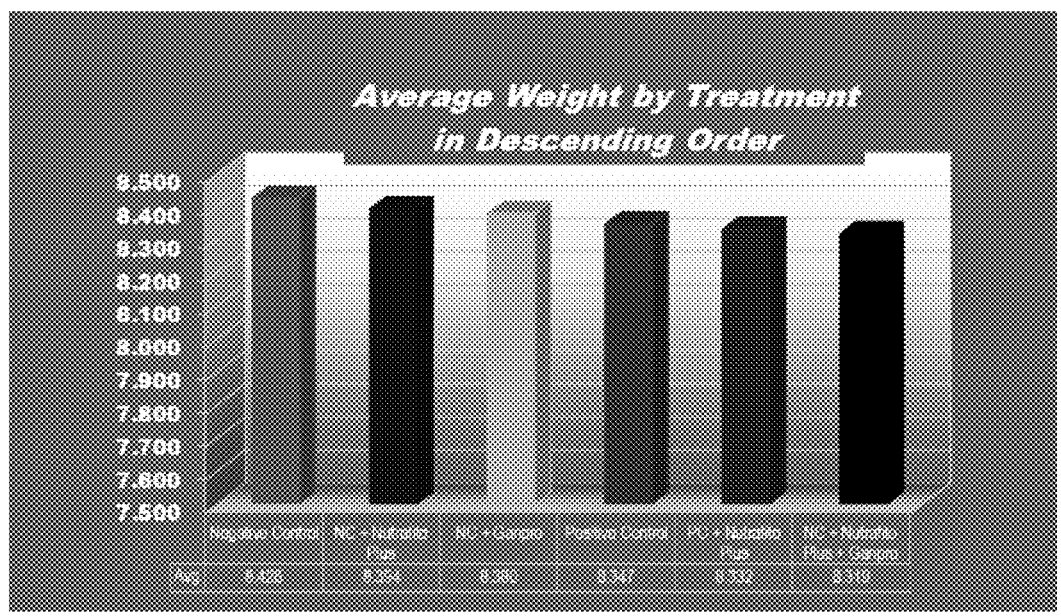
FIG. 2 is a bar graph illustrating average weight results obtained from different types of treatment disclosed herein, with the results organized in descending order (highest average weight to lowest average weight)
Figure 3:
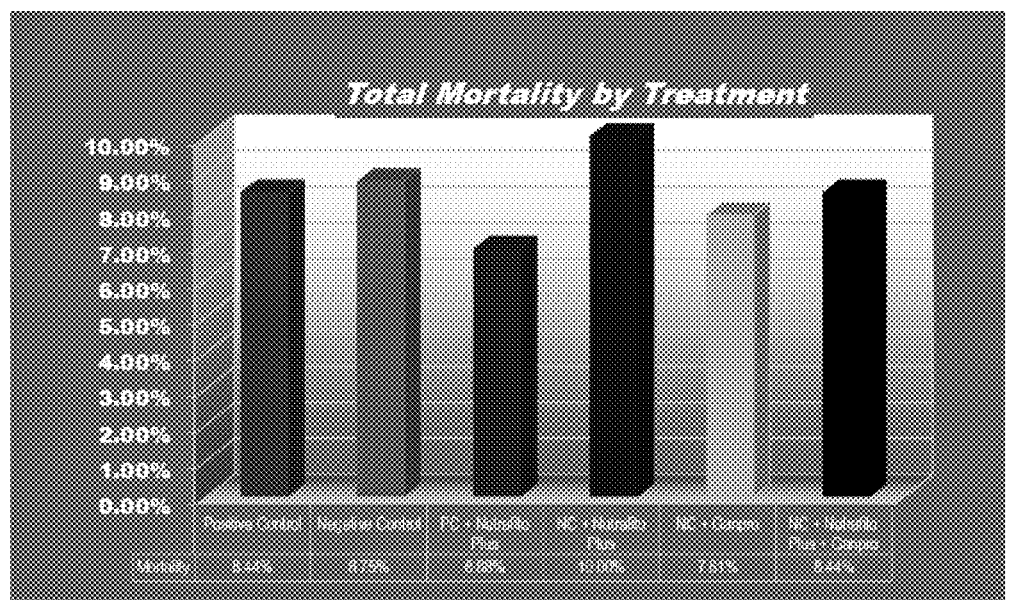
FIG. 3 is a bar graph illustrating total mortality rates obtained with different types of treatment embodiments disclosed herein compared to controls, indicating that there is no substantial difference between the mortality in the control groups, and in the groups fed the disclosed treatments.
Figure 4:
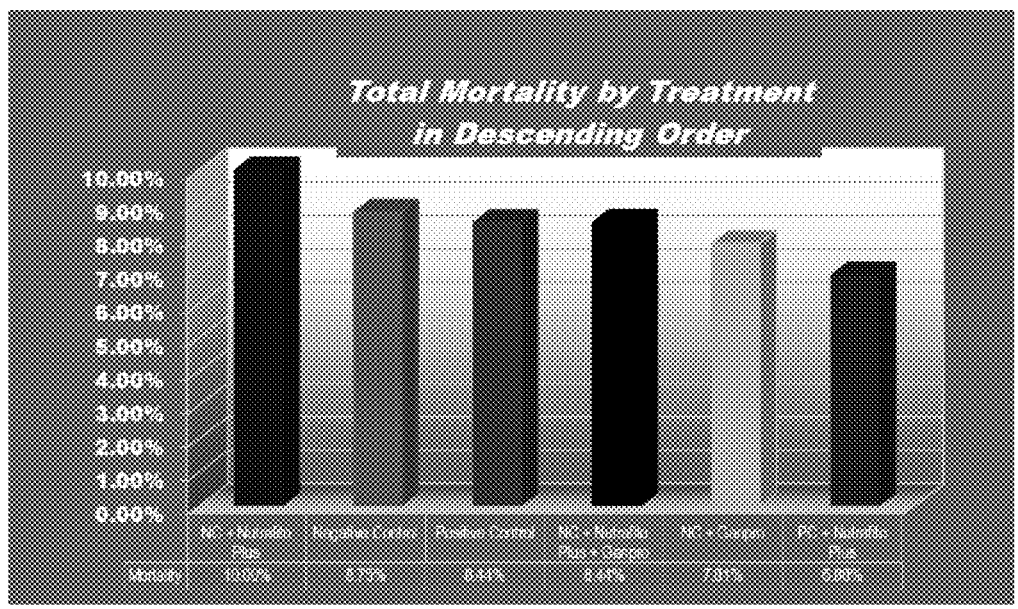
FIG. 4 is a bar graph illustrating total mortality rates obtained with different types of treatment embodiments disclosed herein, with the results organized in descending order (highest mortality rates to lowest mortality rates).
Figure 5:
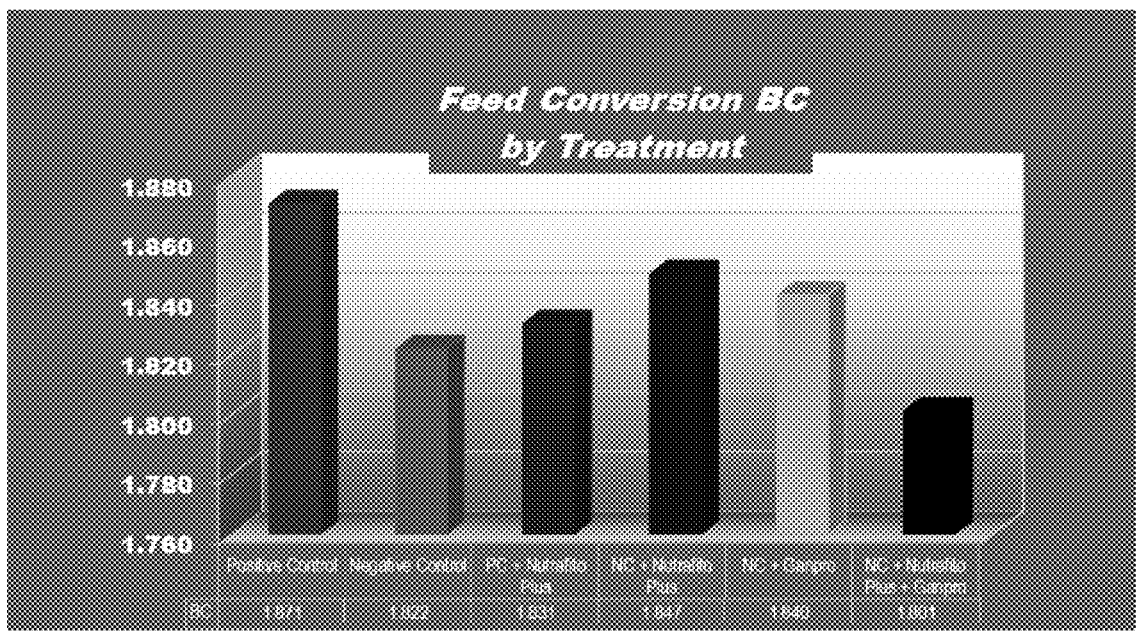
FIG. 5 is a bar graph illustrating feed conversion BC (pounds of feed/pounds of live weight delivered to the plant not including mortality and culls) obtained with different types of treatment embodiments disclosed herein.
Figure 6:
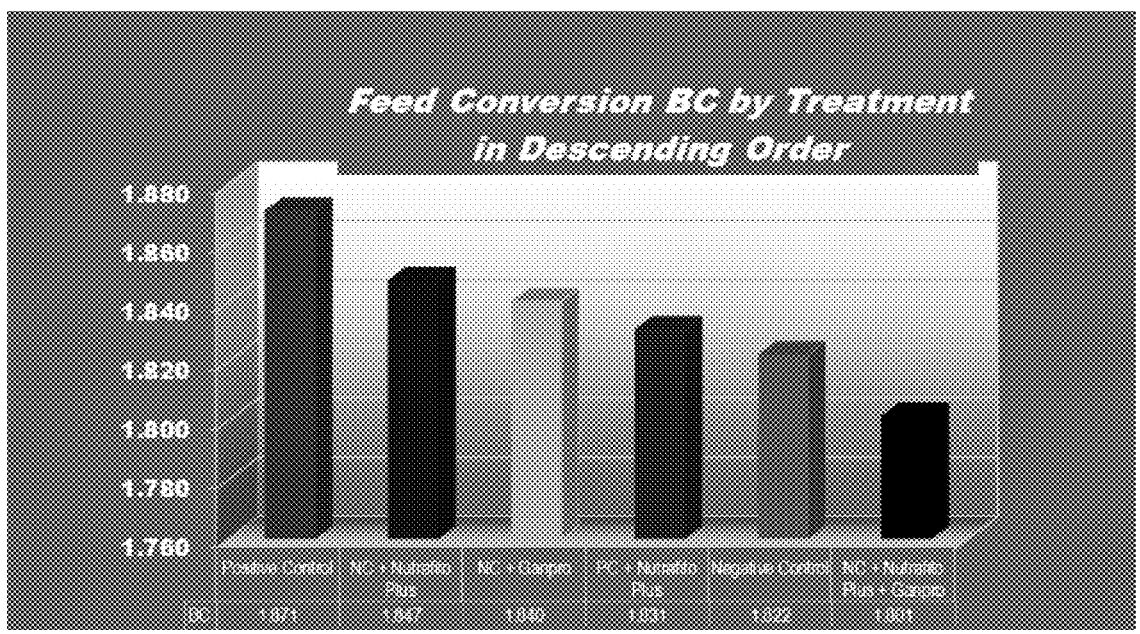
FIG. 6 is a bar graph illustrating feed conversion BC obtained with different types of treatment embodiments disclosed herein, with the results organized in descending order (highest feed conversion BC to lowest feed conversion BC).
Figure 7:
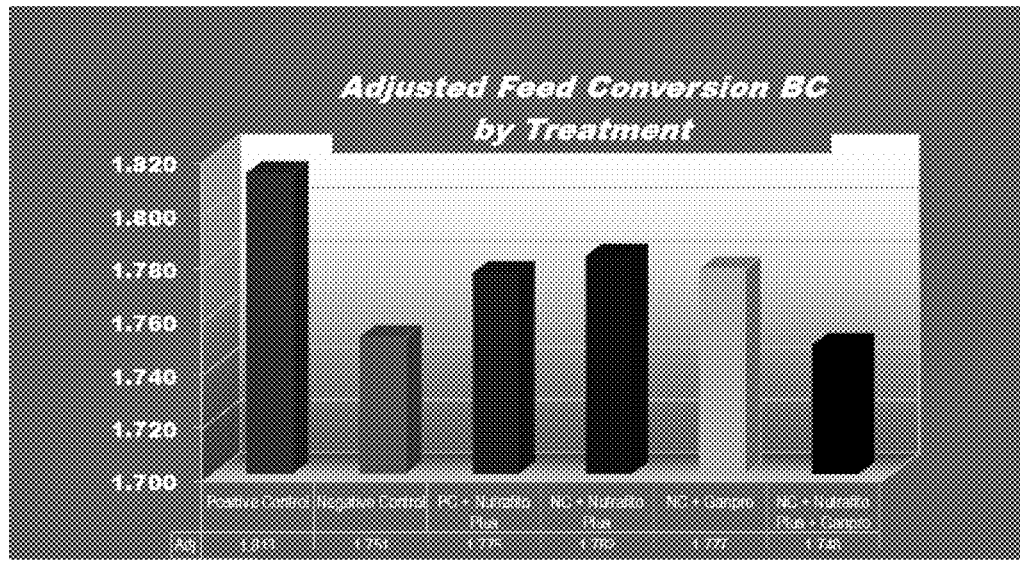
FIG. 7 is a bar graph illustrating adjusted feed conversion BC obtained with different types of treatment embodiments disclosed herein.
Figure 8:
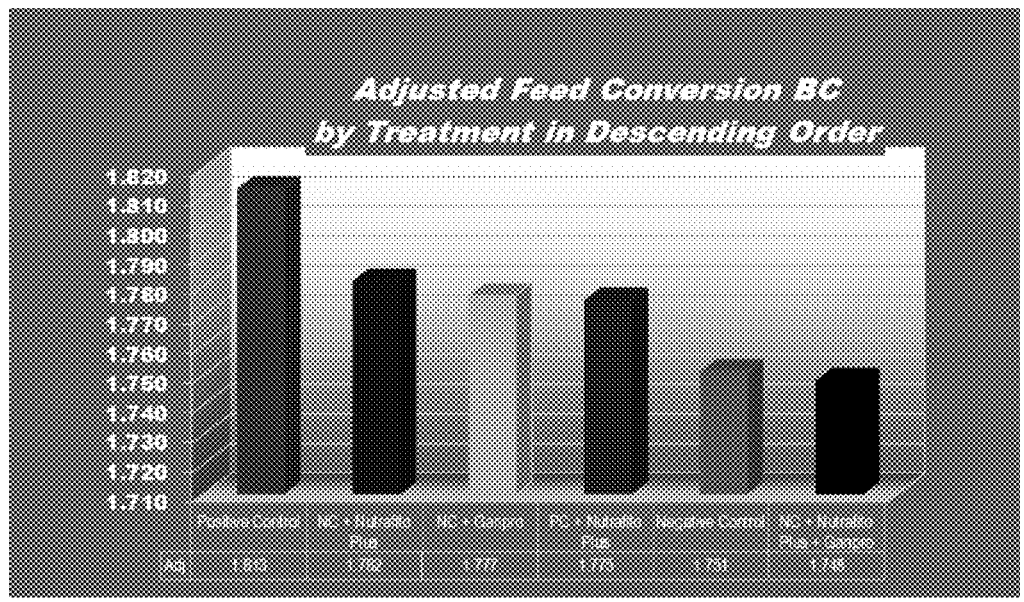
FIG. 8 is a bar graph illustrating adjusted feed conversion BC obtained with different types of treatment embodiments disclosed herein, with the results organized in descending order (highest adjusted feed conversion BC to lowest adjusted feed conversion BC).
Figure 9:
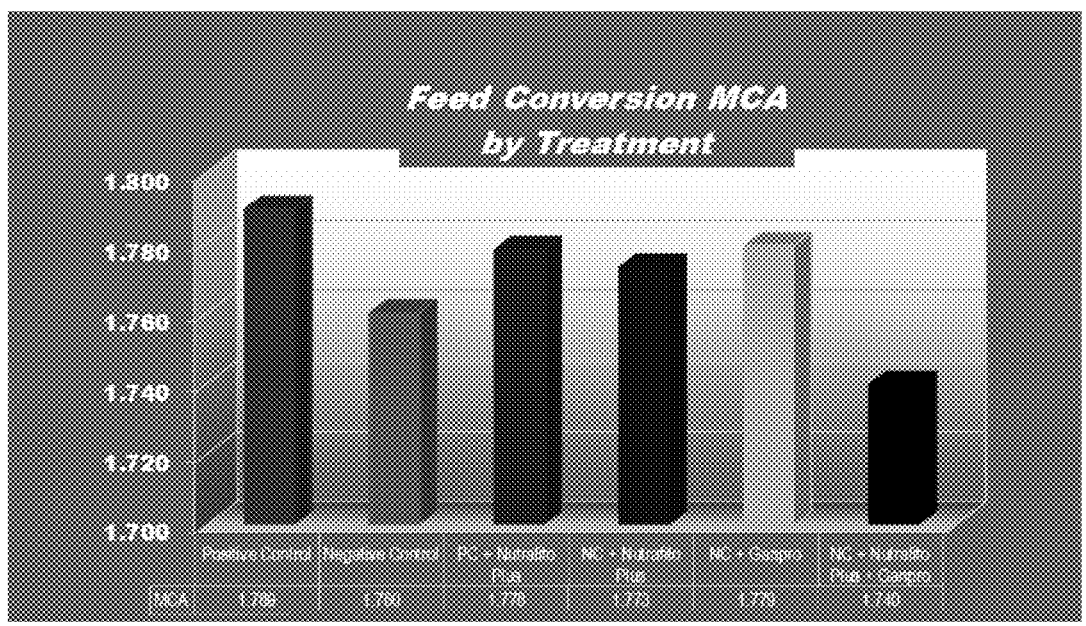
FIG. 9 is a bar graph illustrating feed conversion MCA (feed conversion with mortality and culls—pounds of feed/pounds of live weight and weight of all mortality and culls) obtained with different types of treatment embodiments disclosed herein.
Figure 10:
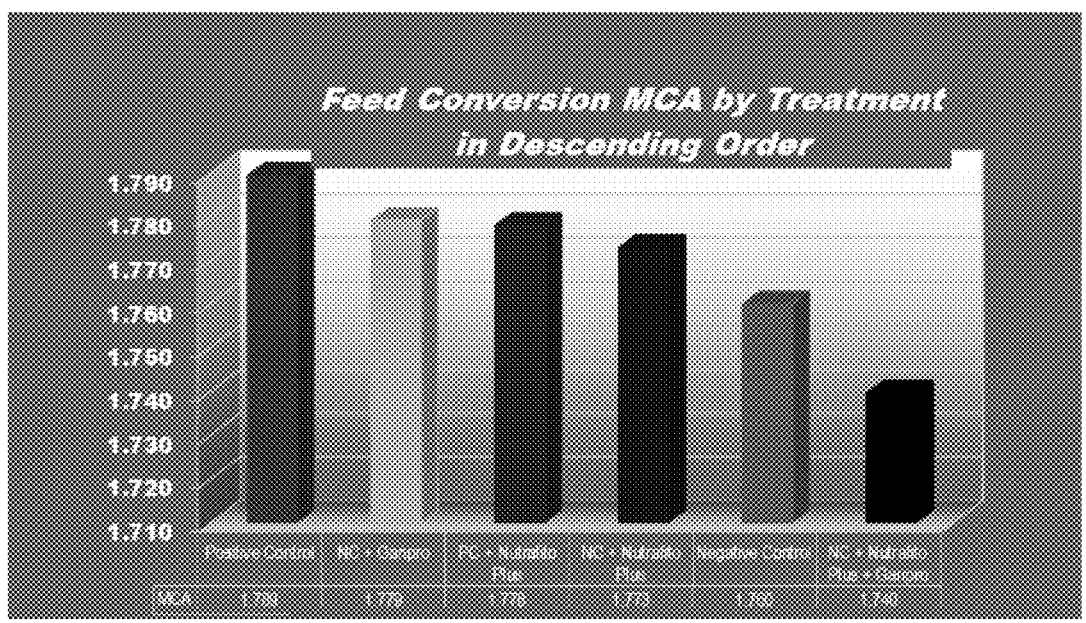
FIG. 10 is a bar graph illustrating feed conversion MCA obtained with different types of treatment embodiments disclosed herein, with the results organized in descending order (highest feed conversion MCA to lowest feed conversion MCA).
Figure 11:
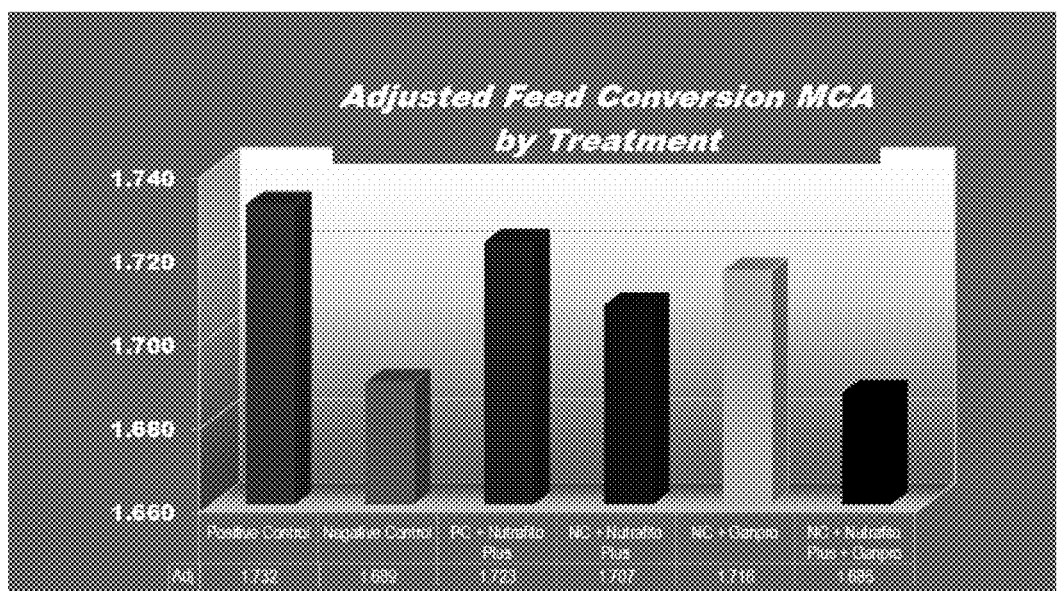
FIG. 11 is a bar graph illustrating adjusted feed conversion MCA obtained with different types of treatment embodiments disclosed herein.
Figure 12:
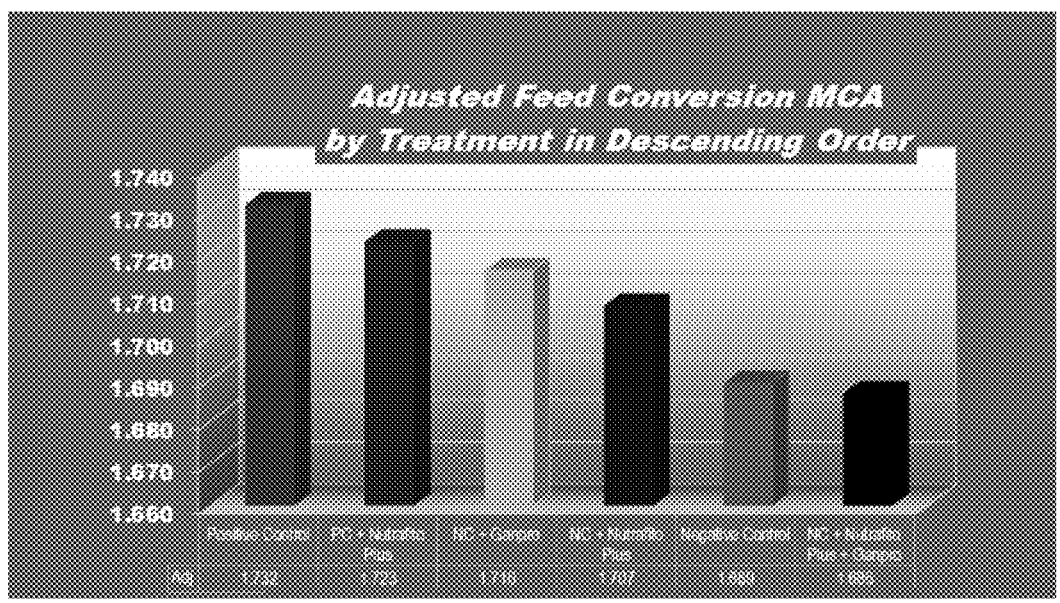
FIG. 12 is a bar graph illustrating adjusted feed conversion MCA obtained with different types of treatment embodiments disclosed herein, with the results organized in descending order (highest adjusted feed conversion MCA to lowest adjusted feed conversion MCA).
Figure 13:
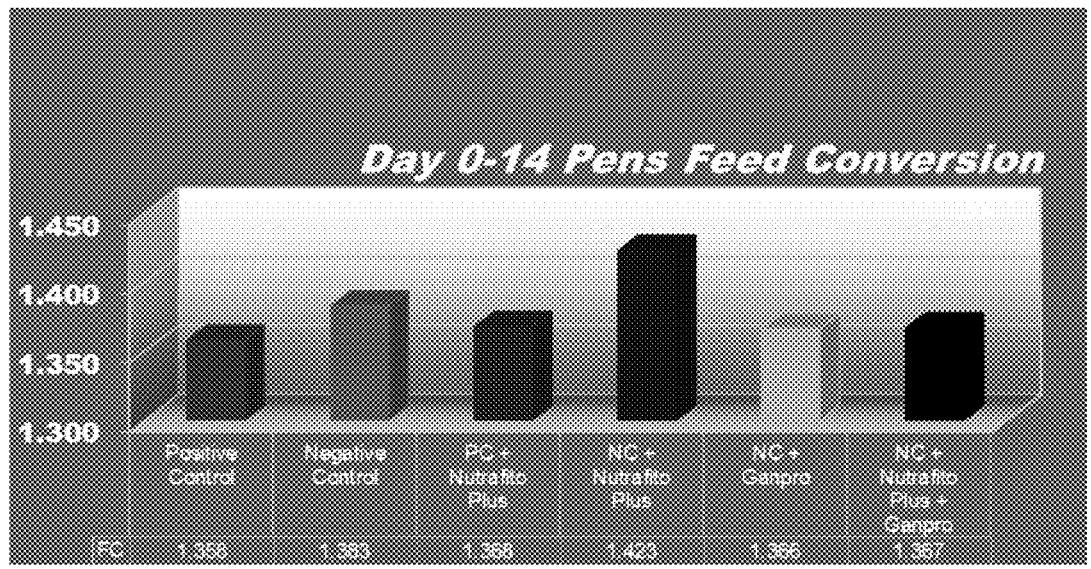
FIG. 13 is a bar graph illustrating results obtained from a 48-day trial wherein feed conversion in chickens in pens was measured after 14 days.
Figure 14:
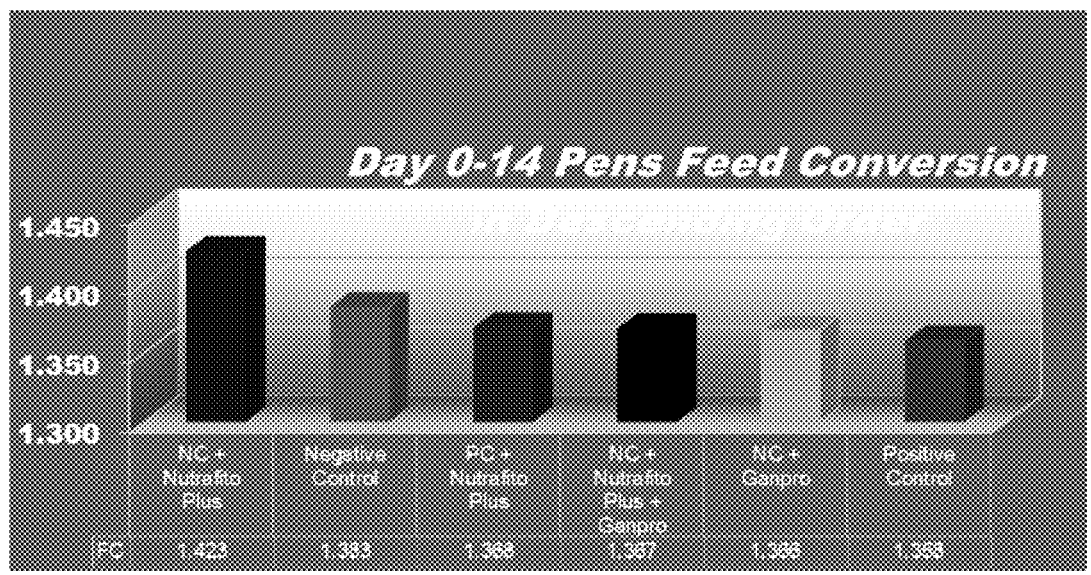
FIG. 14 is a bar graph illustrating results obtained from a 48-day trial wherein feed conversion in chickens in pens was measured after 14 days, wherein the data is provided in descending order (highest feed conversion to lowest feed conversion).
Figure 15:
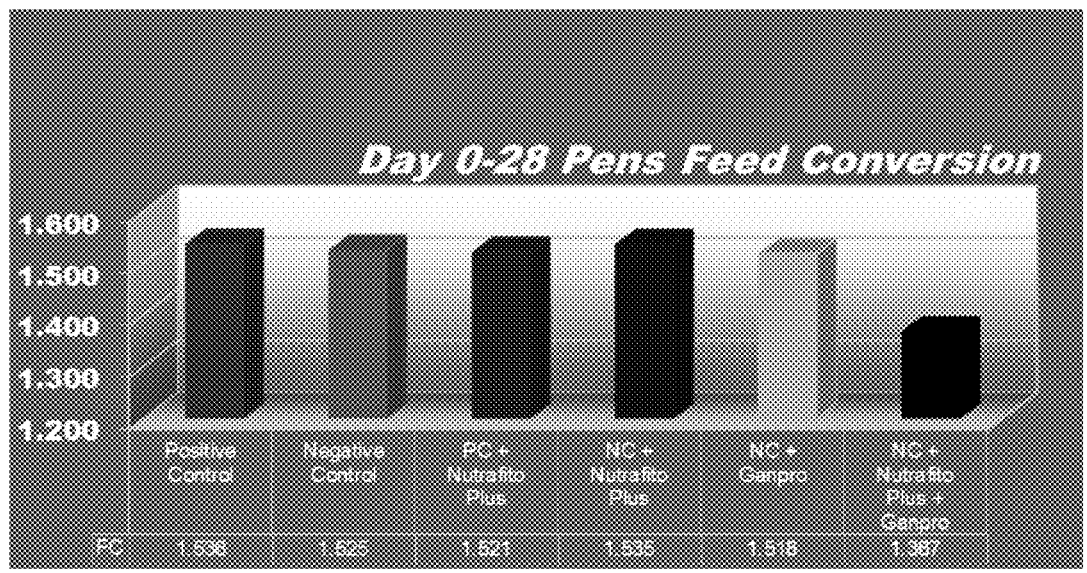
FIG. 15 is a bar graph illustrating results obtained from a 48-day trial wherein feed conversion in chickens in pens was measured after 28 days.
Figure 16:
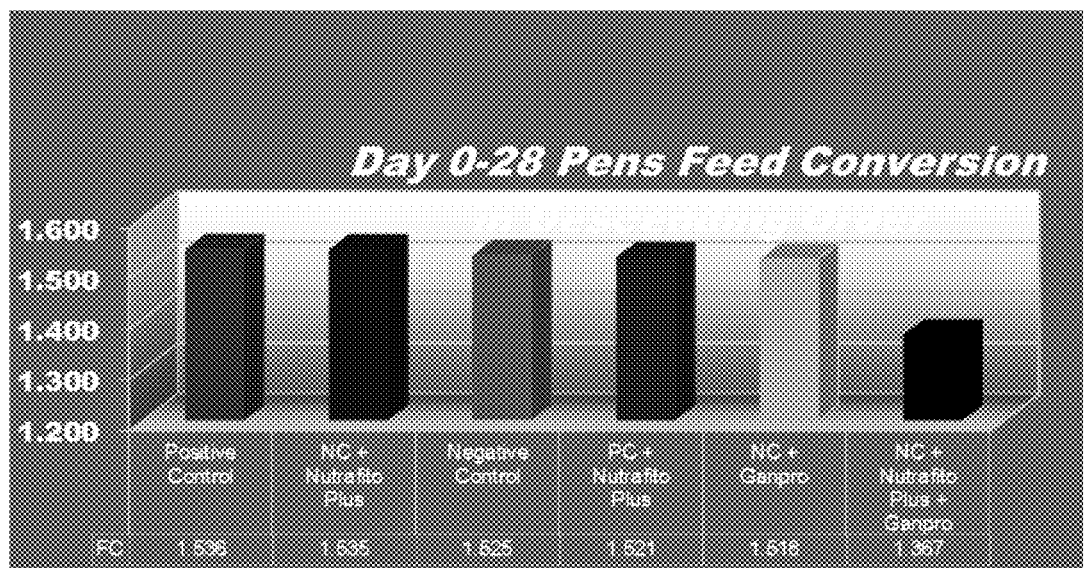
FIG. 16 is a bar graph illustrating results obtained from a 48-day trial wherein feed conversion in chickens in pens was measured after 28 days, wherein the data is provided in descending order (highest feed conversion to lowest feed conversion).
Figure 17:
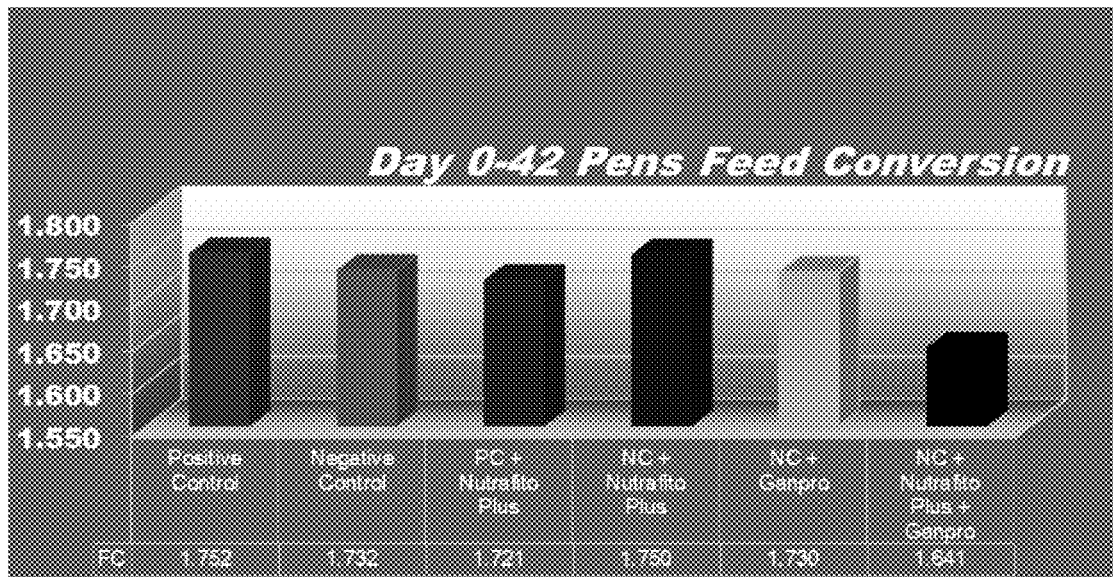
FIG. 17 is a bar graph illustrating results obtained from a 48-day trial wherein feed conversion in chickens in pens was measured after 42 days.
Figure 18:
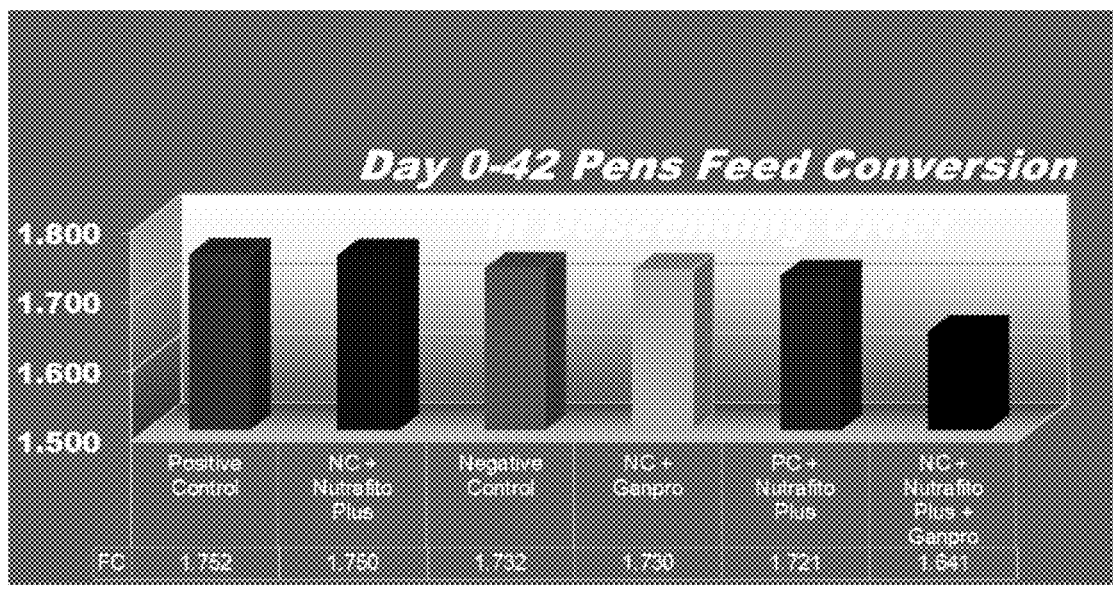
FIG. 18 is a bar graph illustrating results obtained from a 48-day trial wherein feed conversion in chickens in pens was measured after 42 days, wherein the data is provided in descending order (highest feed conversion to lowest feed conversion).
Figure 19:
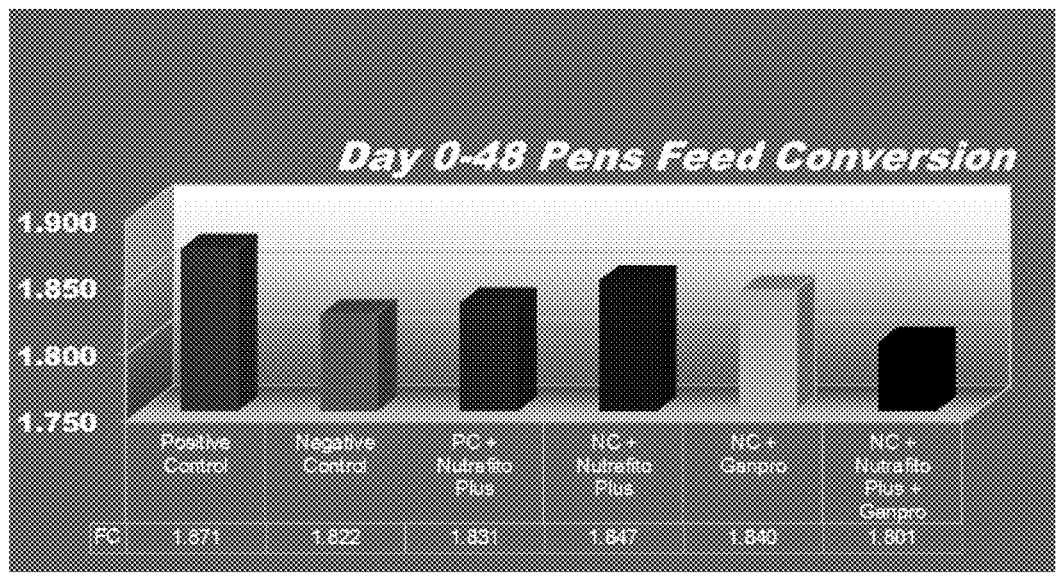
FIG. 19 is a bar graph illustrating results obtained from a 48-day trial wherein feed conversion in chickens in pens was measured after 48 days, clearly indicating the improvement in feed conversion in animal fed the treatment embodiments disclosed herein.
Figure 20:
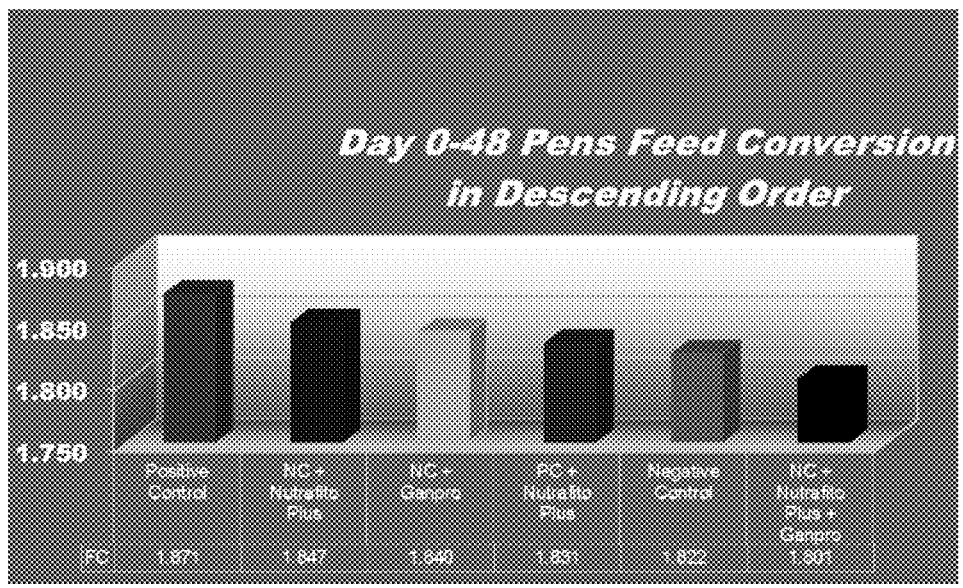
FIG. 20 is a bar graph illustrating results obtained from a 48-day trial wherein feed conversion in chickens in pens was measured after 48 days, wherein the data is provided in descending order (highest feed conversion to lowest feed conversion).
Figure 21:
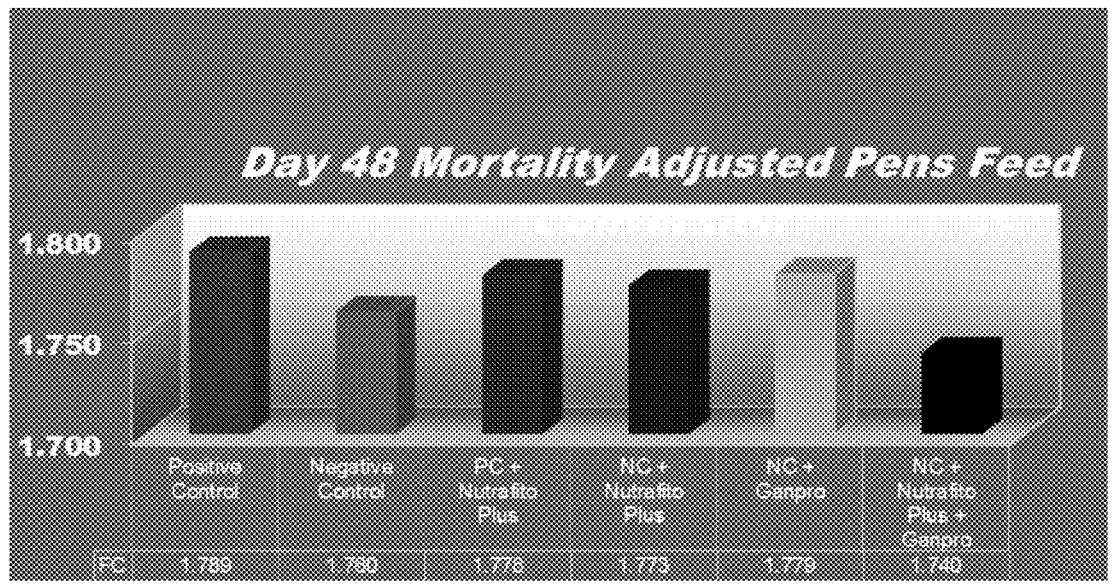
FIG. 21 is a bar graph illustrating results obtained at day 48 of a 48-day trial wherein the mortality adjusted pens feed conversion was measured.
Figure 22:
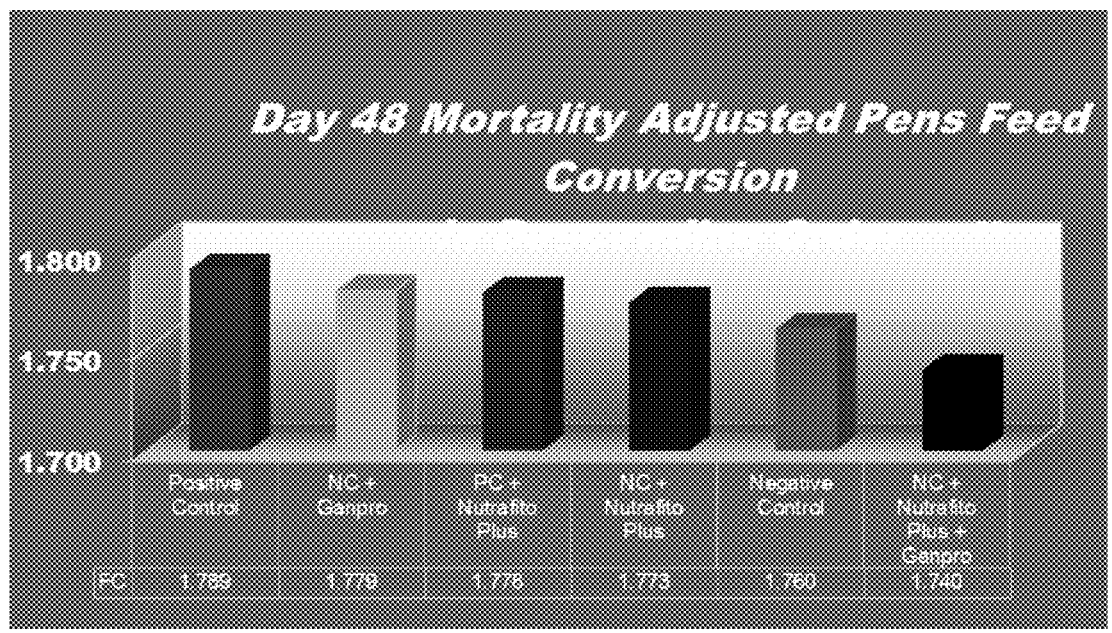
FIG. 22 is a bar graph illustrating results obtained at day 48 of a 48-day trial wherein the mortality adjusted pens feed conversion was measured, with results provided in descending order (highest mortality adjusted feed conversion to lowest mortality adjusted feed conversion).
Figure 24:
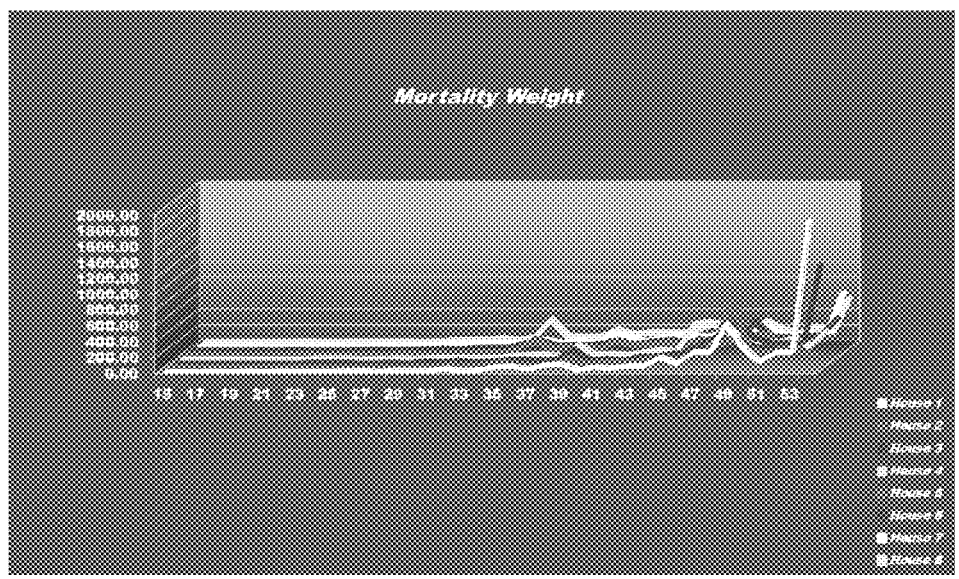
FIG. 24 is a graph (weight versus time [days]) of mortality weight changes over a certain period of time.
Figure 25:
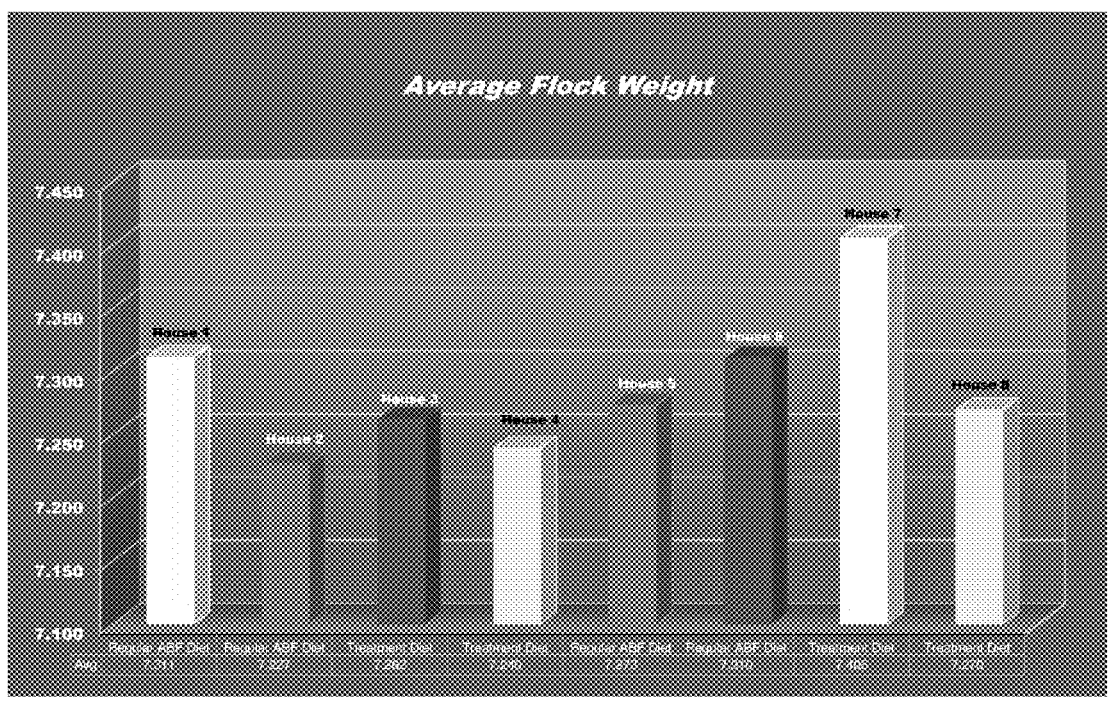
FIG. 25 is a bar graph illustrating average flock weight for different houses wherein either a regular ABF diet or a treatment embodiment as disclosed herein was used.
Figure 26:
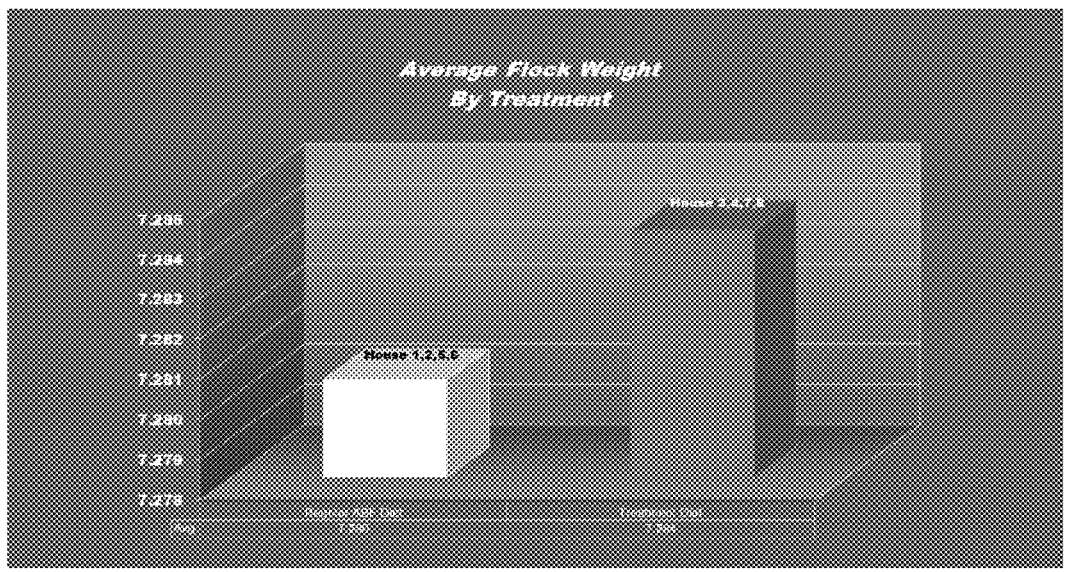
FIG. 26 is a bar graph illustrating average flock weight based on the type of treatment used (regular ABF diet versus a treatment embodiment disclosed herein).
Figure 27:
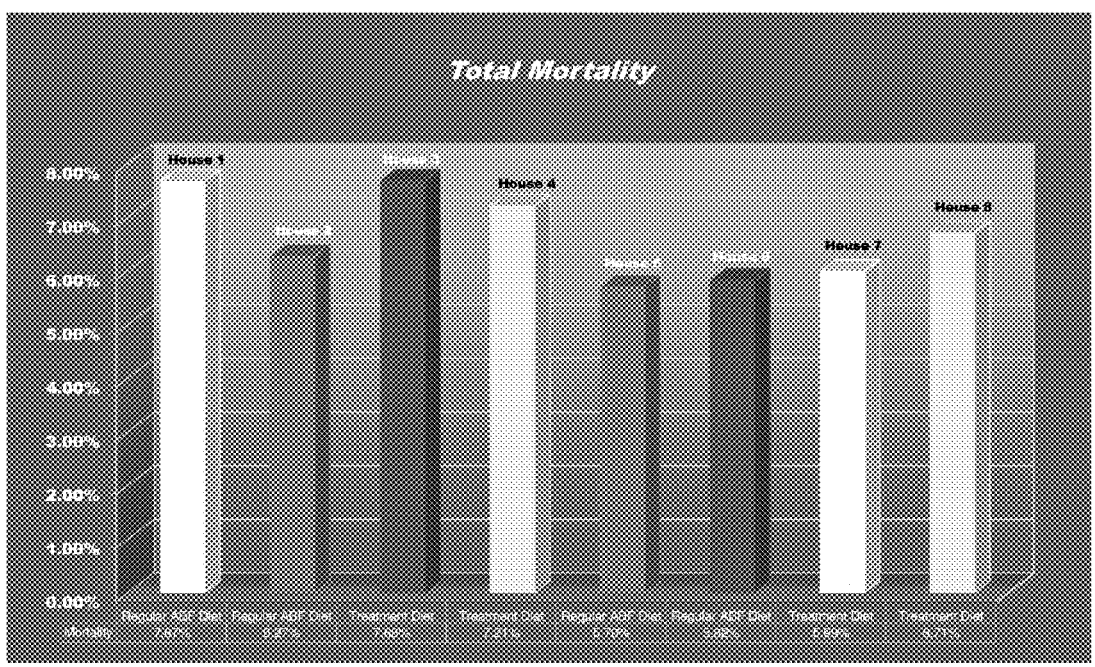
FIG. 27 is a bar graph illustrating total mortality (as percentage) for different houses wherein either a regular ABF diet or a treatment embodiment as disclosed herein was used. In some embodiments, groups fed the treatments disclosed herein had lower mortality rates than the control groups. In embodiments where the mortality was higher, the differences were not substantial.
Figure 28:
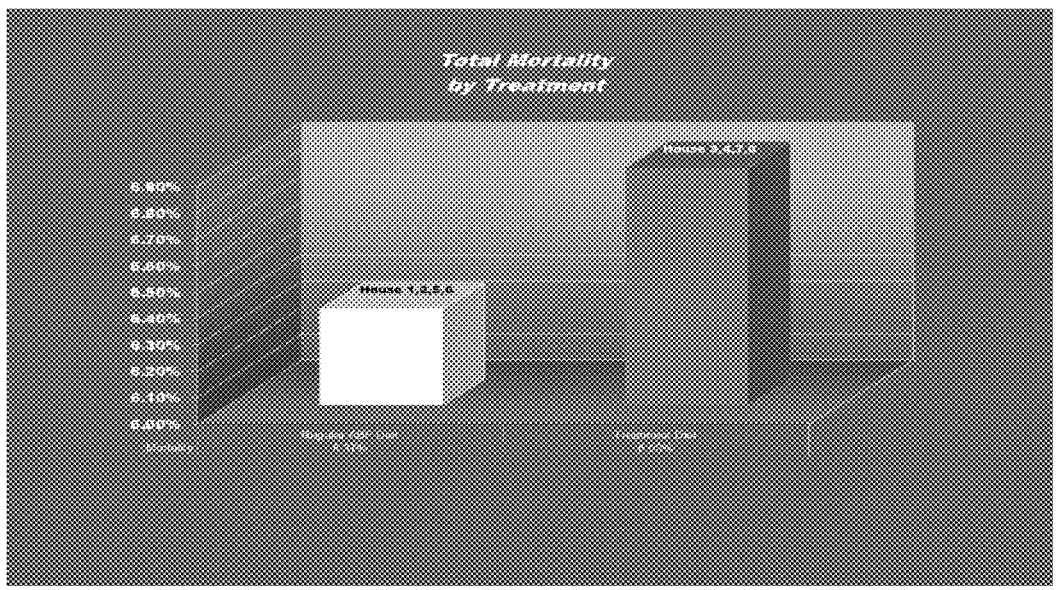
FIG. 28 is a bar graph illustrating total mortality based on the type of treatment used (regular ABF diet versus a treatment embodiment disclosed herein).
Figure 29:
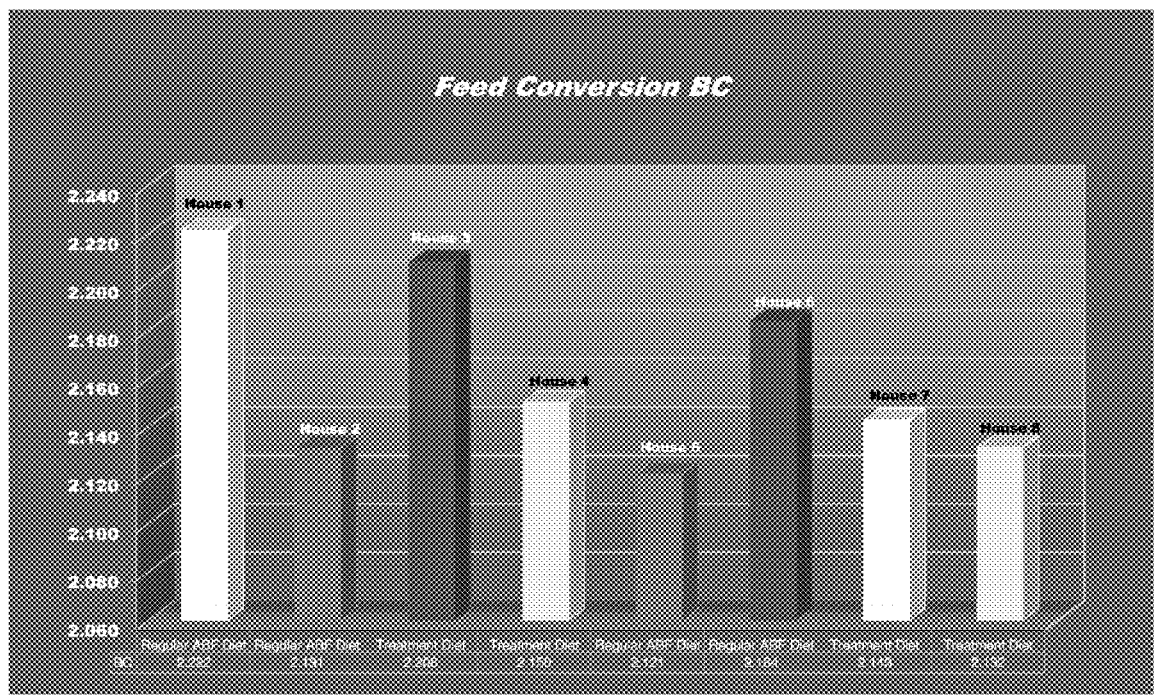
FIG. 29 is a bar graph illustrating feed conversion BC for different houses wherein either a regular ABF diet or a treatment embodiment as disclosed herein was used.
Figure 30:
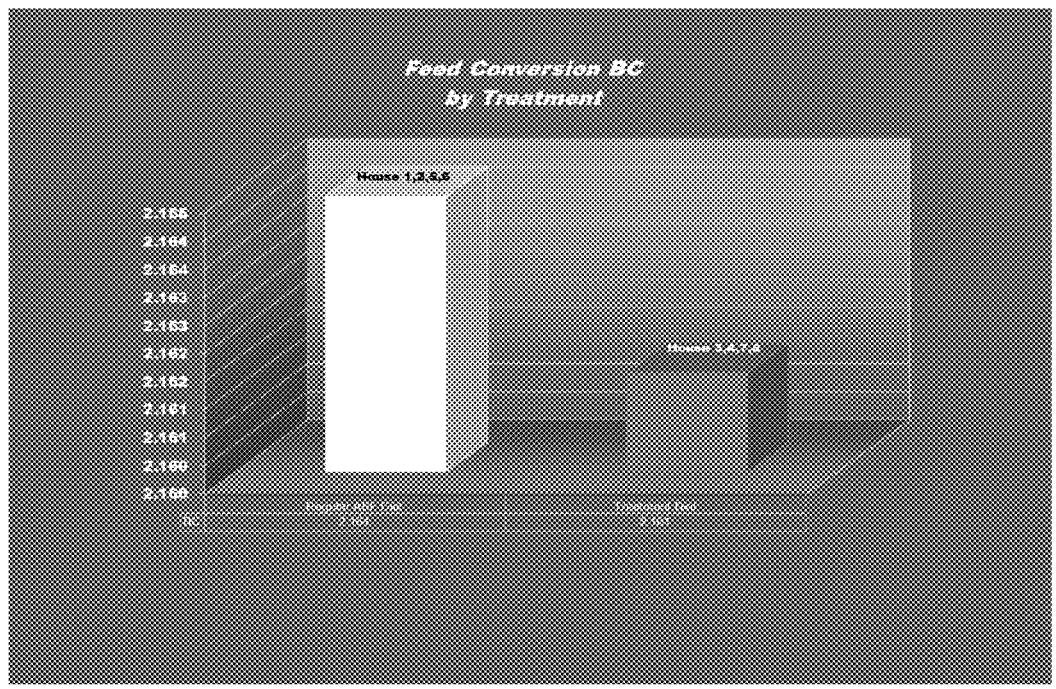
FIG. 30 is a bar graph illustrating feed conversion BC based on the type of treatment used (regular ABF diet versus a treatment embodiment disclosed herein).
Figure 31:
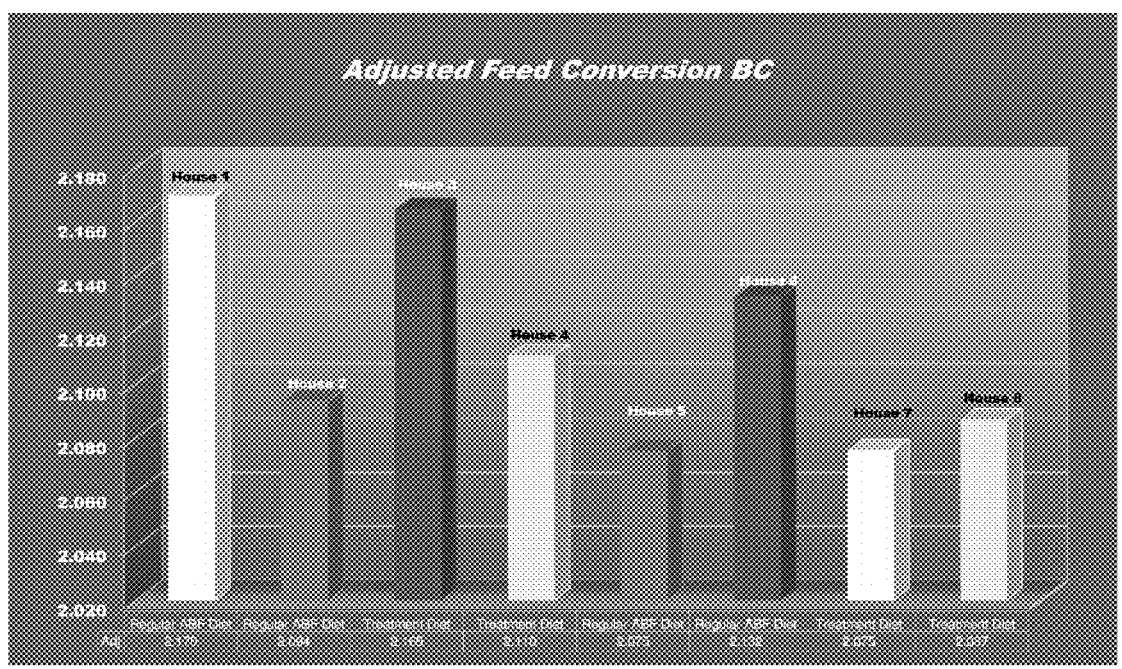
FIG. 31 is a bar graph illustrating adjusted feed conversion BC for different houses wherein either a regular ABF diet or a treatment embodiment as disclosed herein was used.
Figure 32:
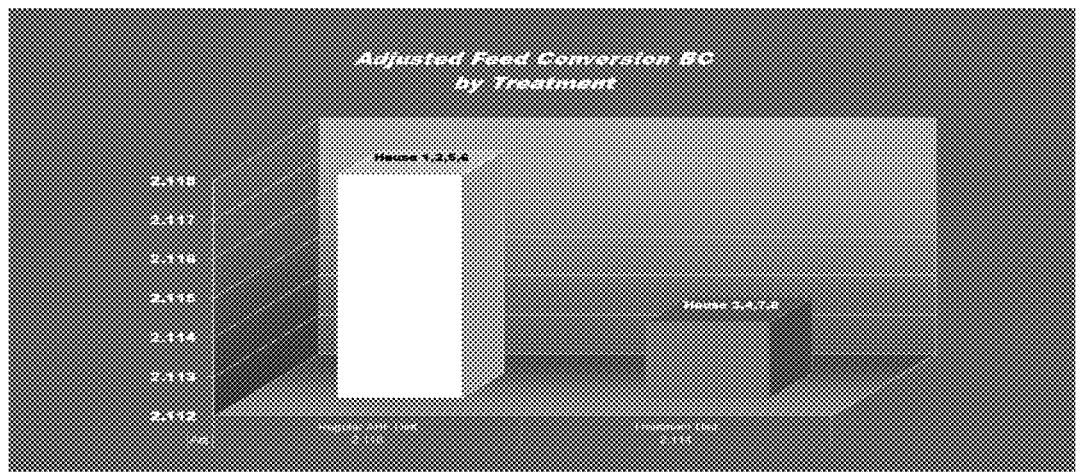
FIG. 32 is a bar graph illustrating adjusted feed conversion BC based on the type of treatment used (regular ABF diet versus a treatment embodiment disclosed herein).
Figure 33:
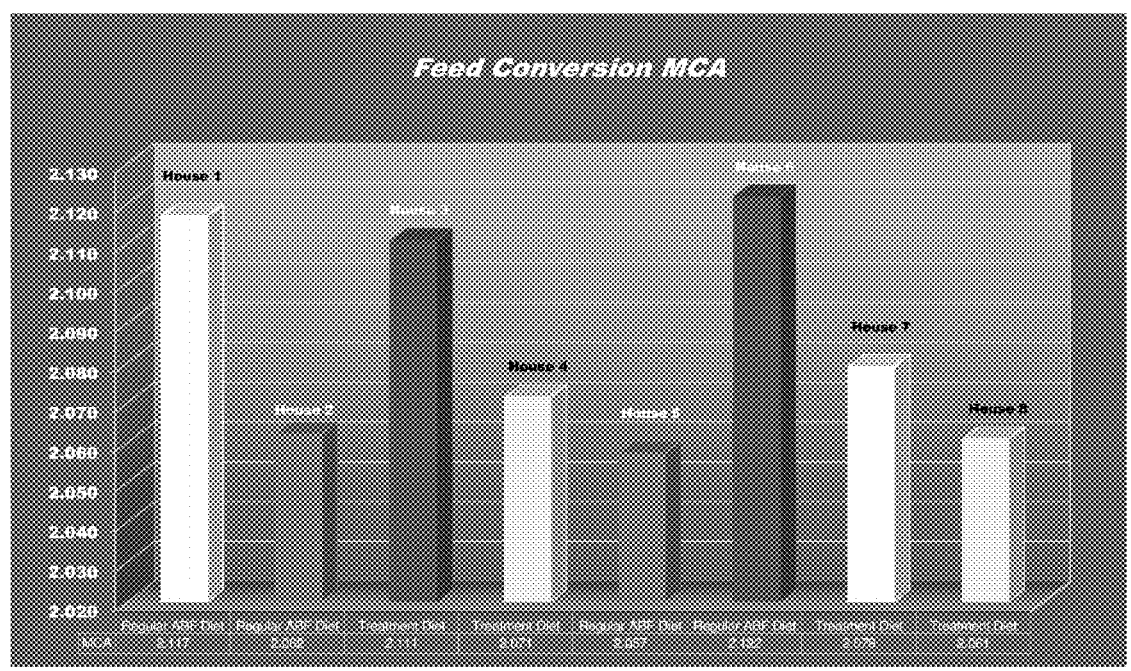
FIG. 33 is a bar graph illustrating feed conversion MCA for different houses wherein either a regular ABF diet or a treatment embodiment as disclosed herein was used.
Figure 34:
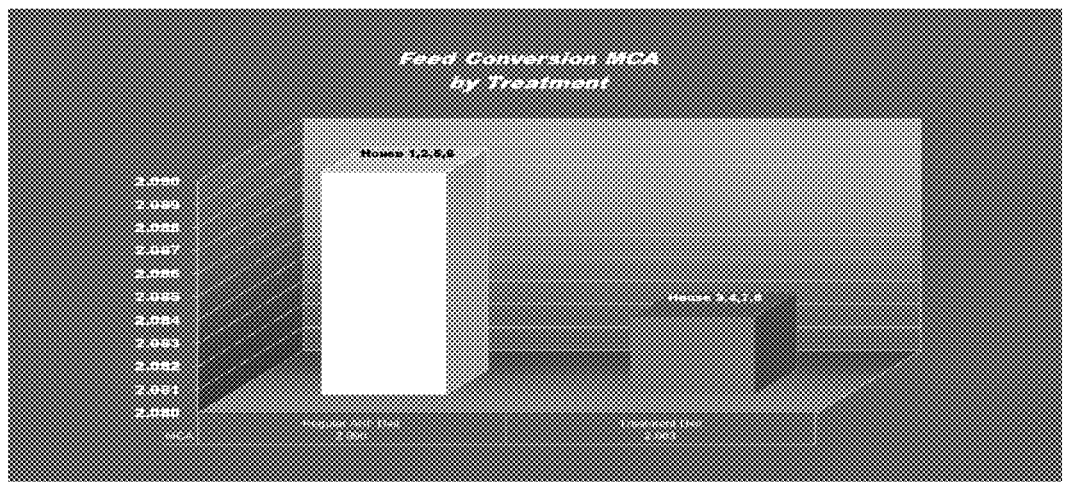
FIG. 34 is a bar graph illustrating feed conversion MCA based on the type of treatment used (regular ABF diet versus a treatment embodiment disclosed herein).
Figure 35:
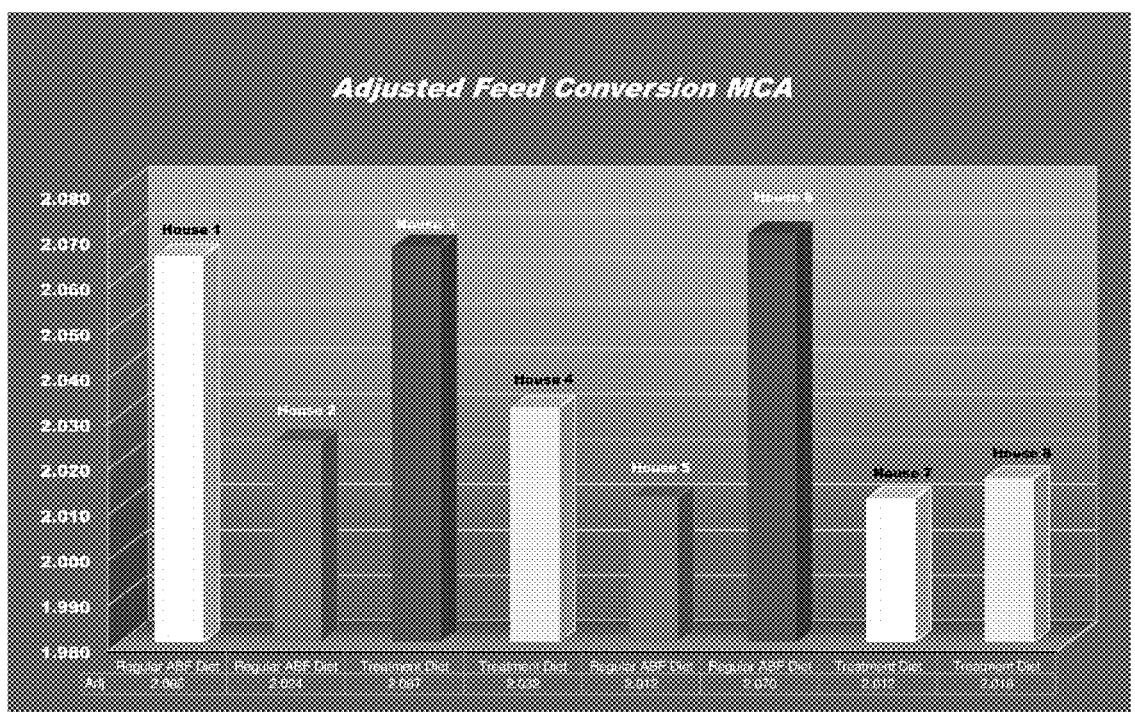
FIG. 35 is a bar graph illustrating adjusted feed conversion MCA for different houses wherein either a regular ABF diet or a treatment embodiment as disclosed herein was used.
Figure 36:
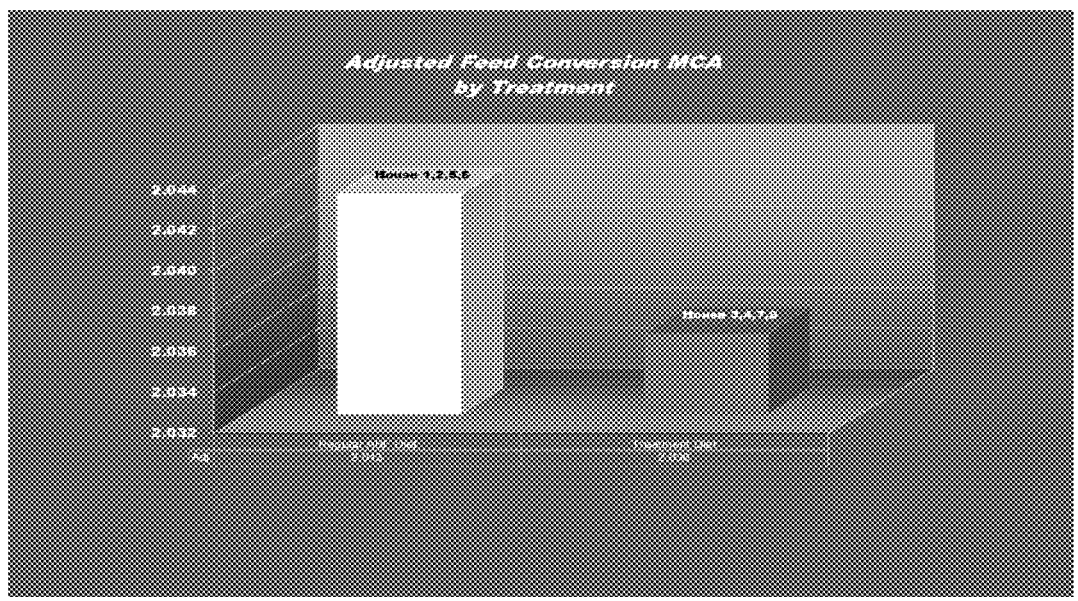
FIG. 36 is a bar graph illustrating adjusted feed conversion MCA based on the type of treatment used (regular ABF diet versus a treatment embodiment disclosed herein).
Figure 37:
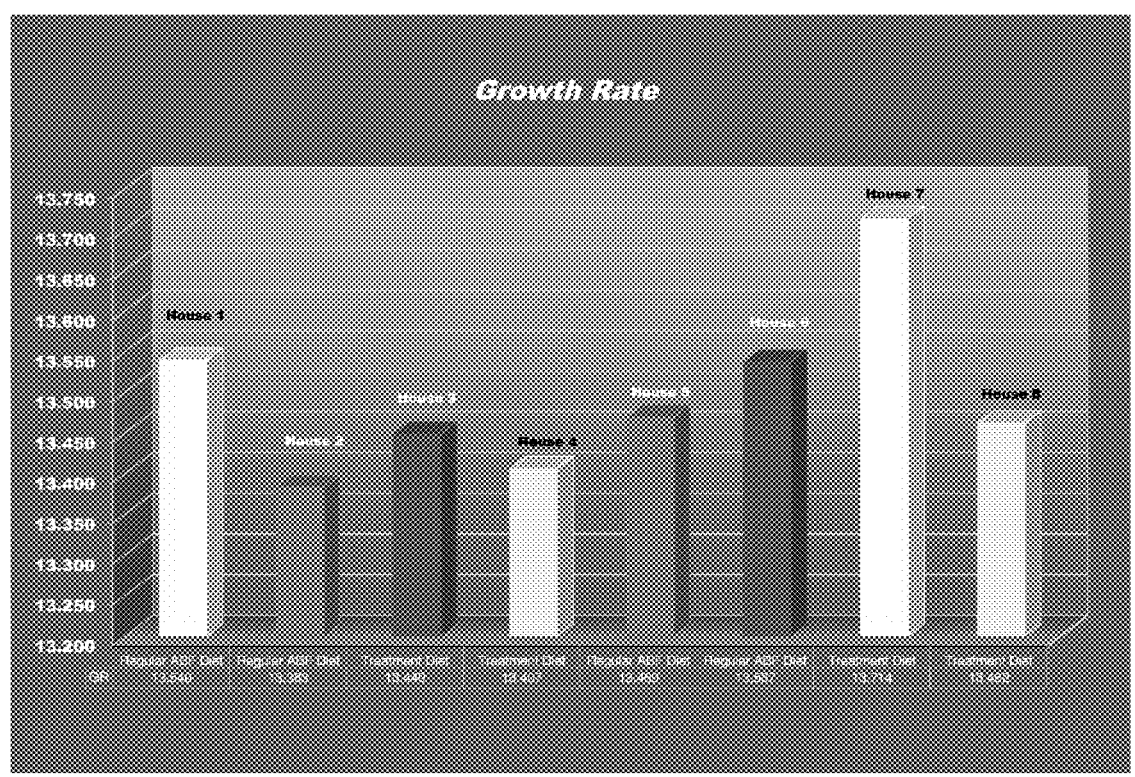
FIG. 37 is a bar graph illustrating growth rate for different houses wherein either a regular ABF diet or a treatment embodiment as disclosed herein was used.
Figure 38:
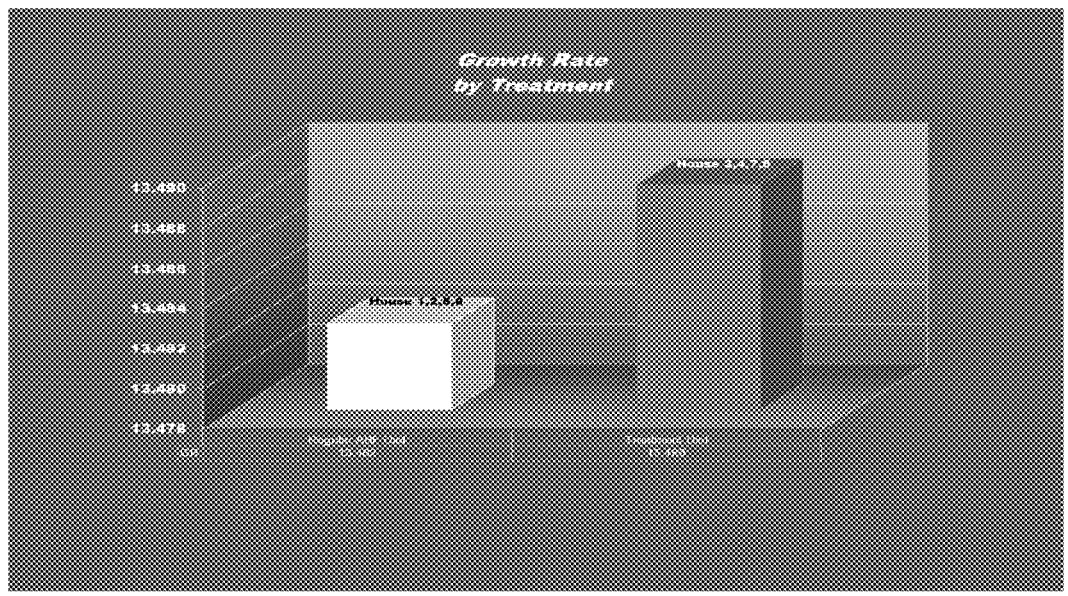
FIG. 38 is a bar graph illustrating growth rate based on the type of treatment used (regular ABF diet versus a treatment embodiment disclosed herein).
Figure 39:
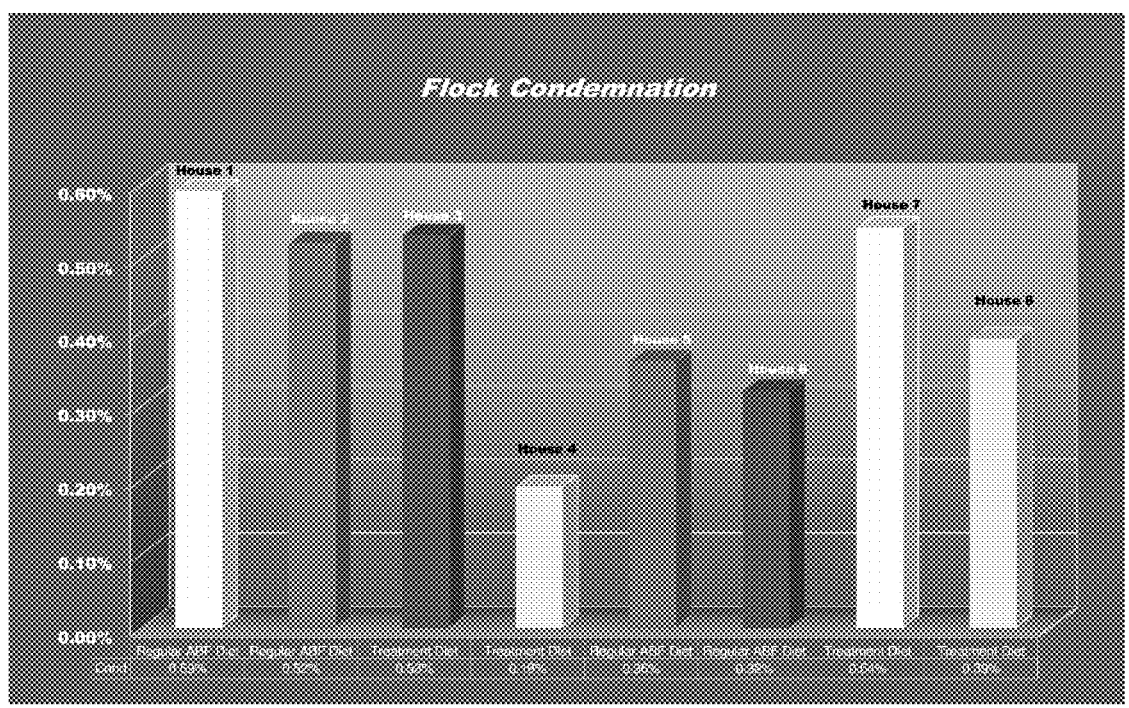
FIG. 39 is a bar graph illustrating flock condemnation for different houses wherein either a regular ABF diet or a treatment embodiment as disclosed herein was used.
Figure 40:
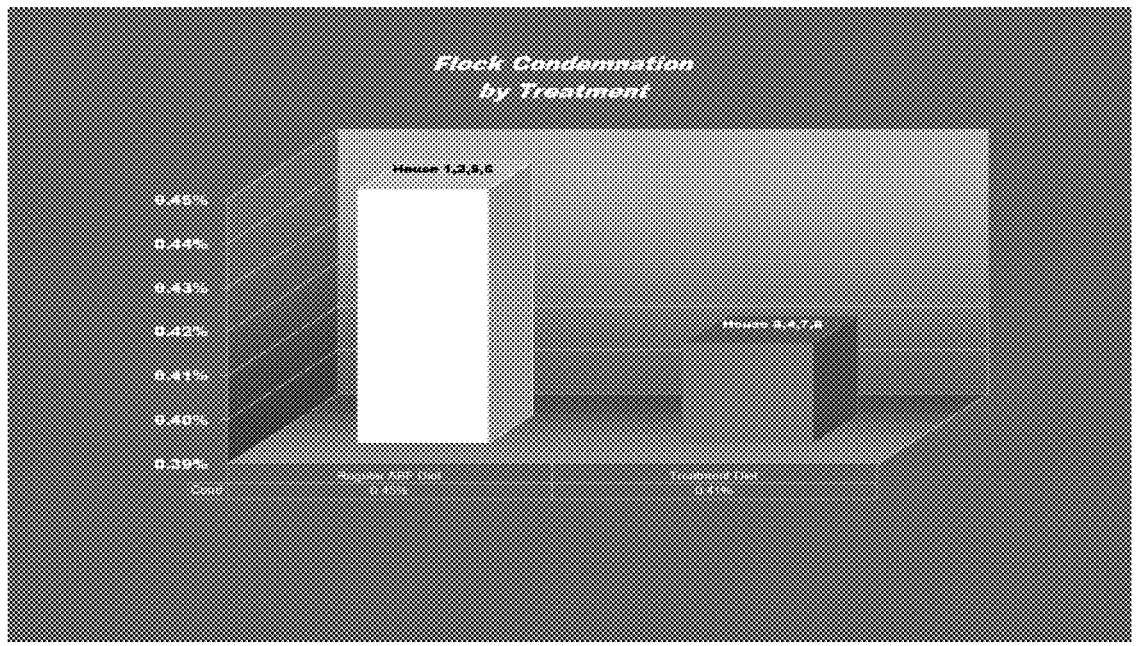
FIG. 40 is a bar graph illustrating flock condemnation based on the type of treatment used (regular ABF diet versus a treatment embodiment disclosed herein).
Figure 41:
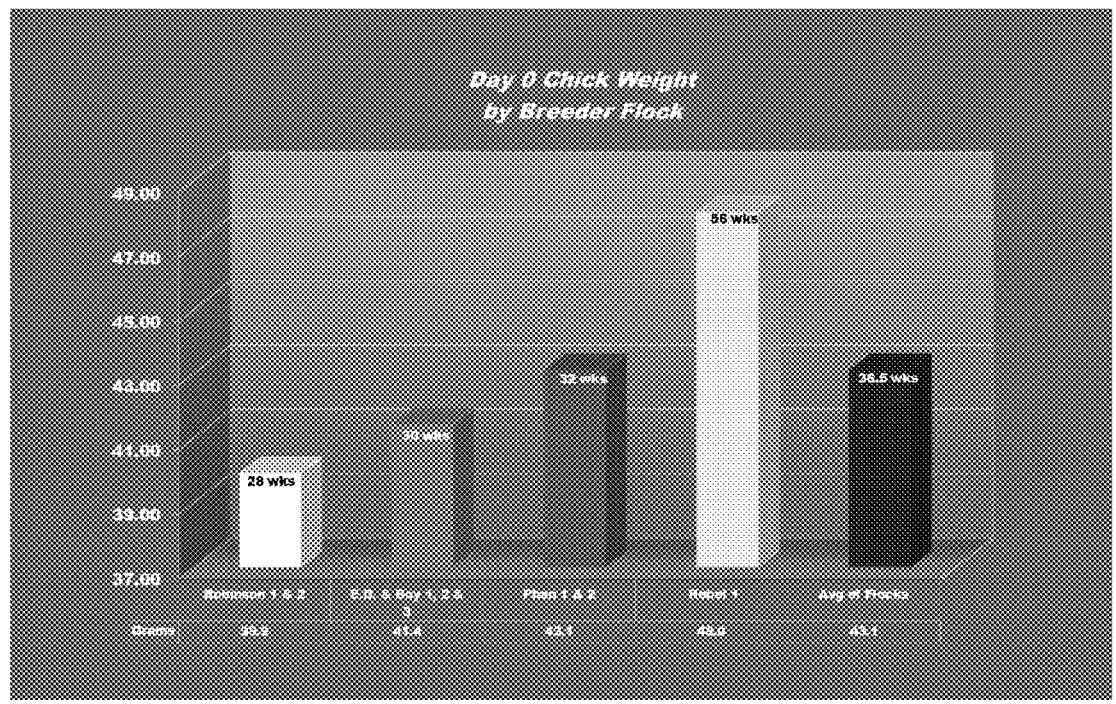
FIG. 41 is a bar graph of chick weight (grams) at the start of a 48-day trial, with each bar corresponding to the weight of a different type of breeder flock, including a bar representing an average of the flocks.
Figure 42:
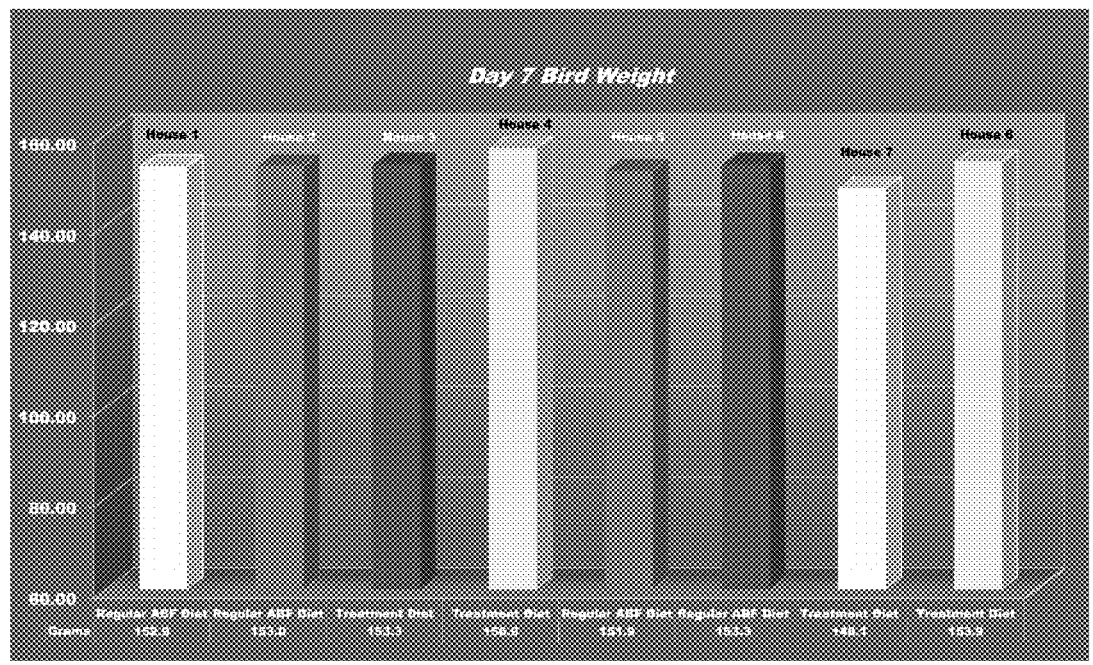
FIG. 42 is a bar graph of bird weight (grams) measured at day 7 of the 48-day trial for different houses wherein either a regular ABF diet or a treatment embodiment as disclosed herein was used.
Figure 43:
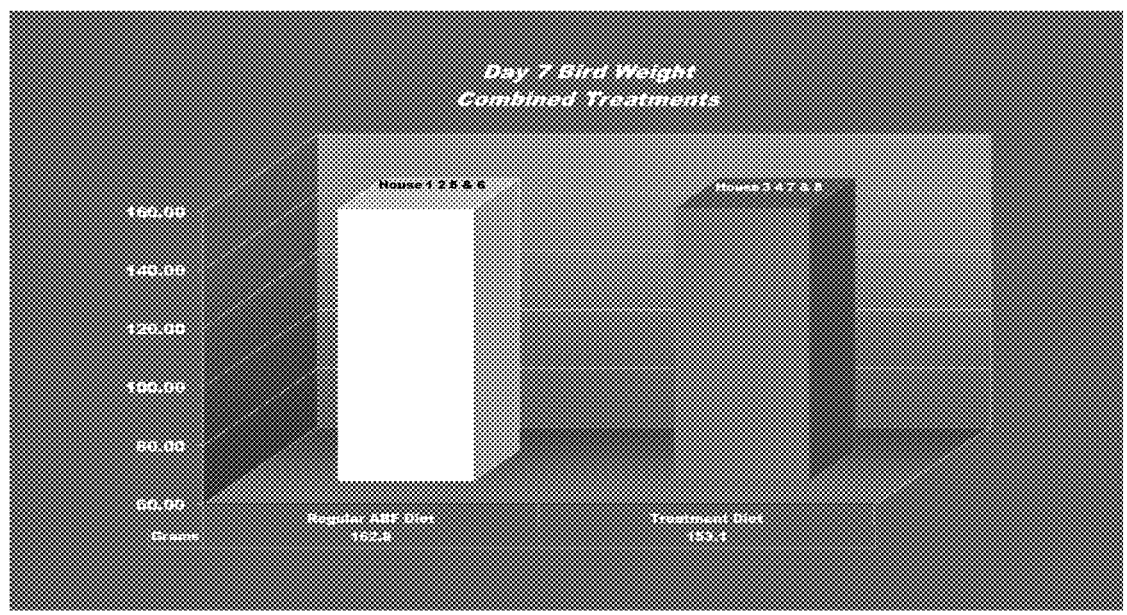
FIG. 43 is a bar graph illustrating bird weight (grams) measured at day 7 of the 48-day trial with the measurements based on the type of treatment used (regular ABF diet versus a treatment embodiment disclosed herein).
Figure 44:
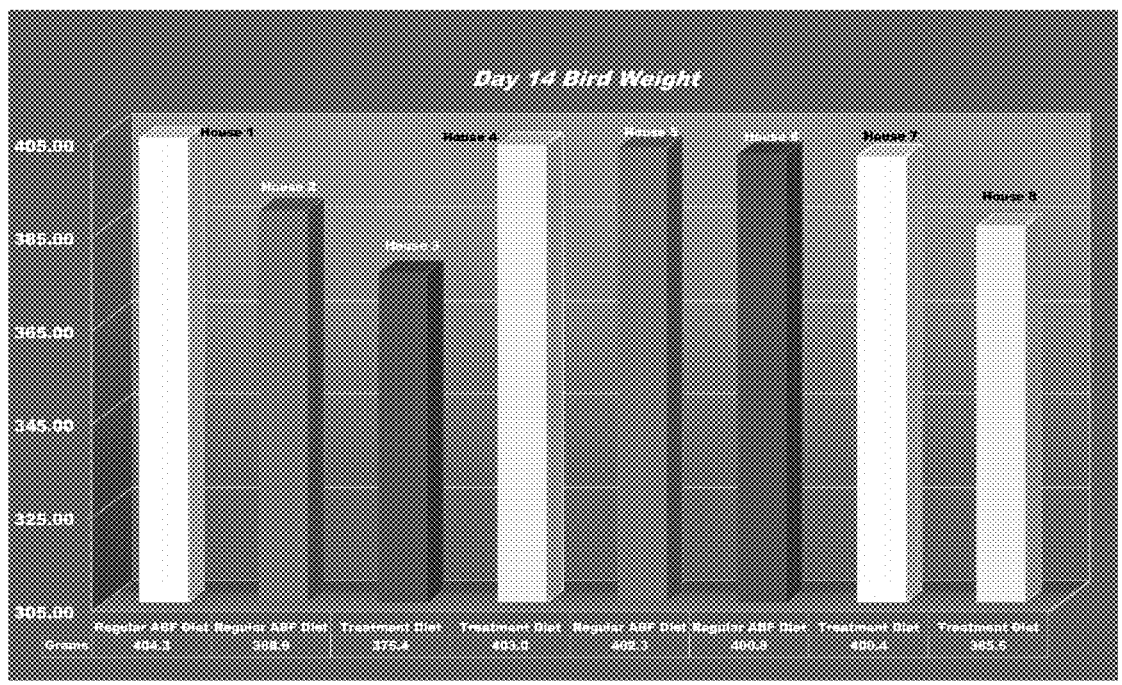
FIG. 44 is a bar graph of bird weight (grams) measured at day 14 of the 48-day trial for different houses wherein either a regular ABF diet or a treatment embodiment as disclosed herein was used.
Figure 45:
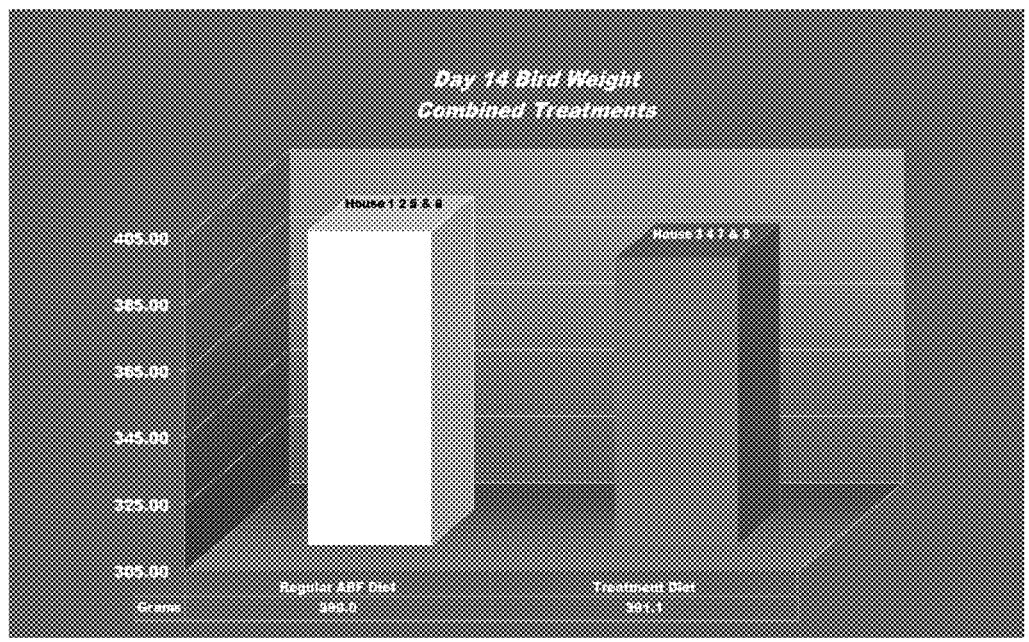
FIG. 45 is a bar graph illustrating bird weight (grams) measured at day 14 of the 48-day trial with the measurements based on the type of treatment used (regular ABF diet versus a treatment embodiment disclosed herein).
Figure 46:
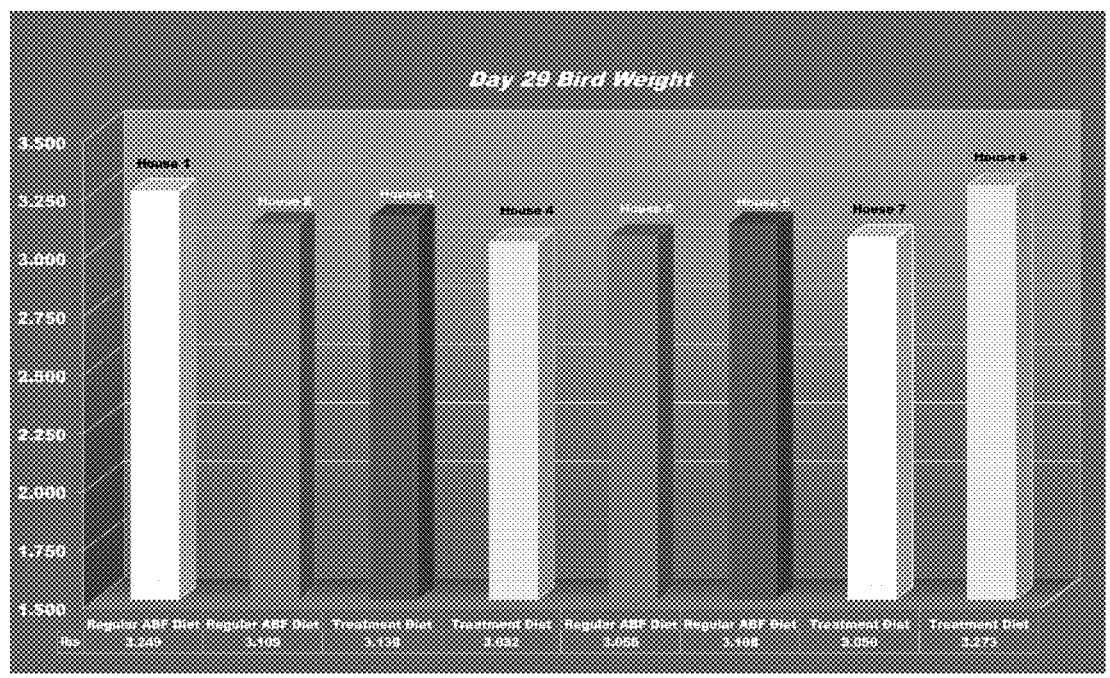
FIG. 46 is a bar graph of bird weight (grams) measured at day 29 of the 48-day trial for different houses wherein either a regular ABF diet or a treatment embodiment as disclosed herein was used.
Figure 47:
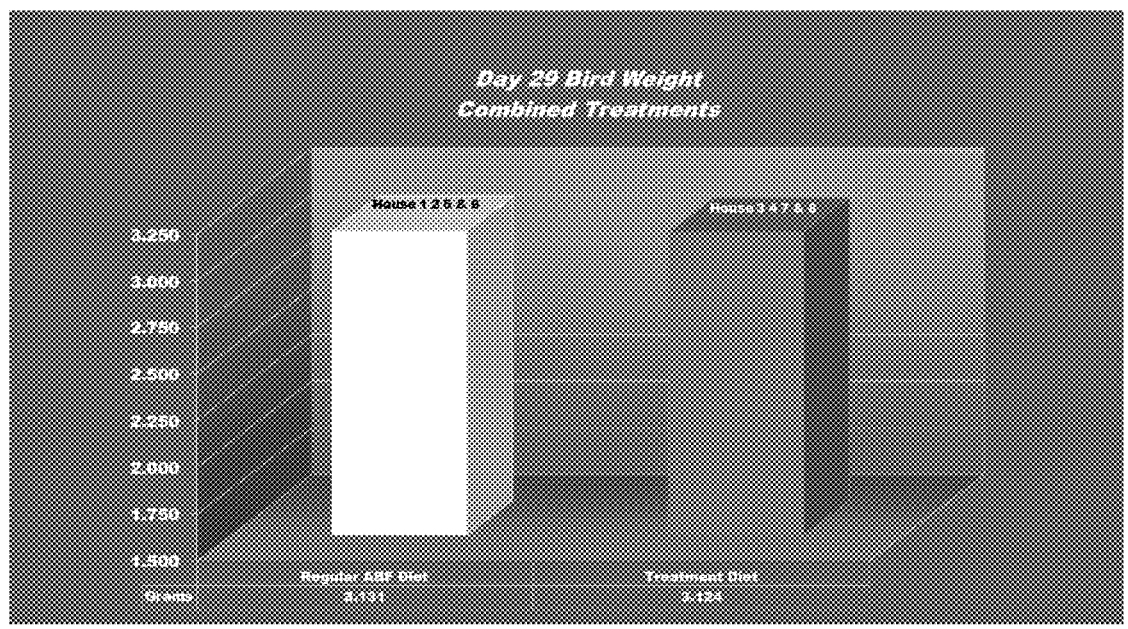
FIG. 47 is a bar graph illustrating bird weight (grams) measured at day 29 of the 48-day trial with the measurements based on the type of treatment used (regular ABF diet versus a treatment embodiment disclosed herein).
Figure 48:
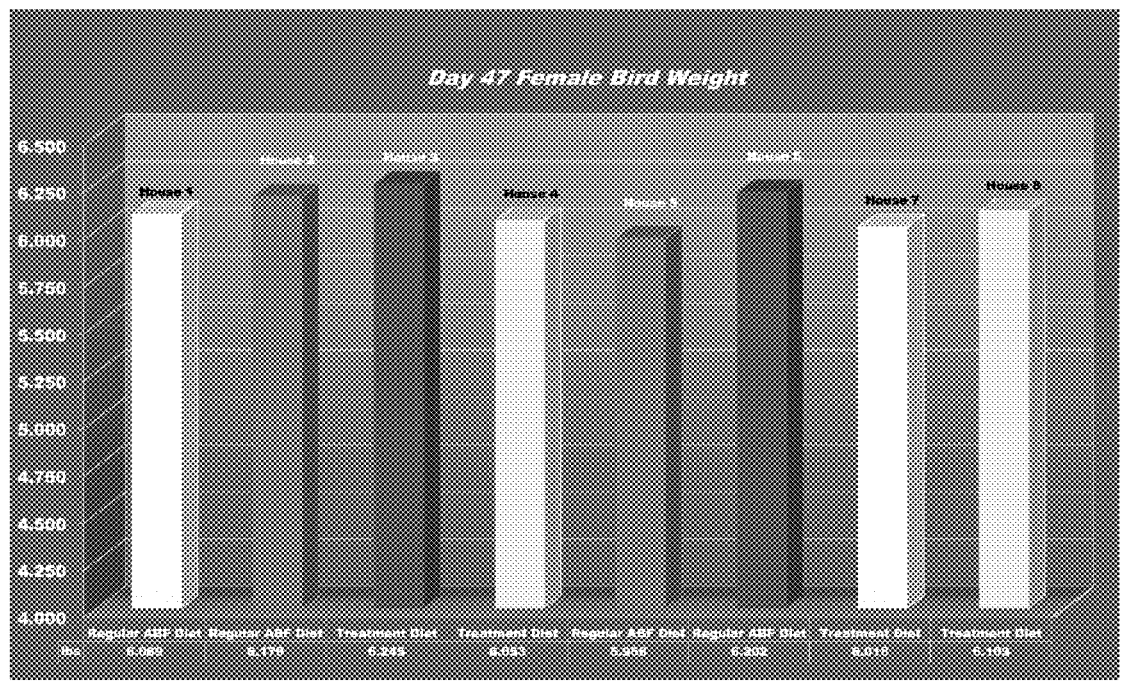
FIG. 48 is a bar graph of female bird weight (grams) measured at day 47 of the 48-day trial for different houses wherein either a regular ABF diet or a treatment embodiment as disclosed herein was used.
Figure 49:
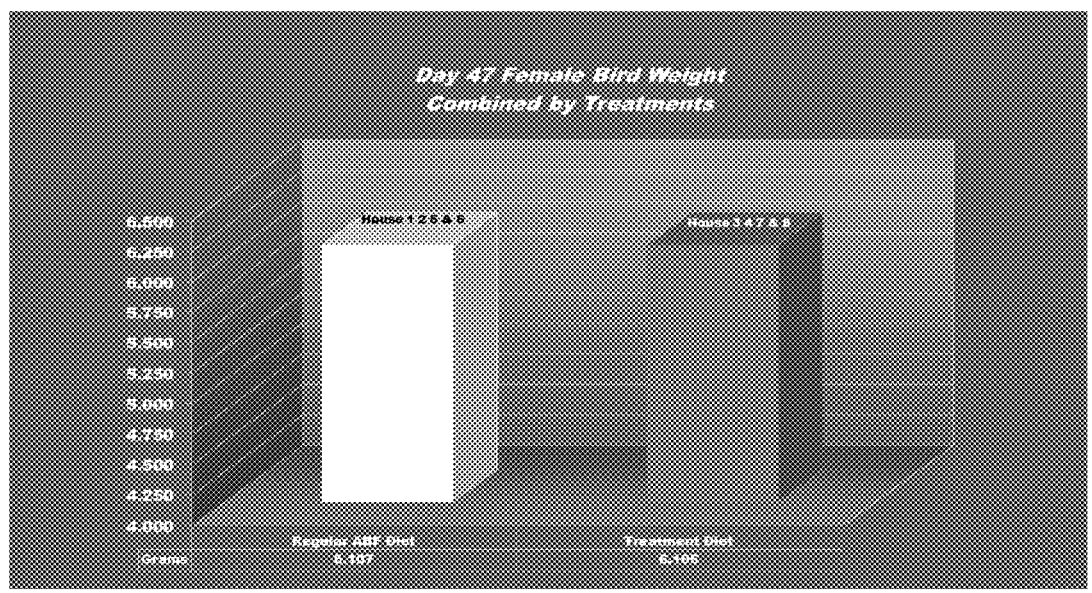
FIG. 49 is a bar graph illustrating female bird weight (grams) measured at day 47 of the 48-day trial with the measurements based on the type of treatment used (regular ABF diet versus a treatment embodiment disclosed herein).
Figure 50:
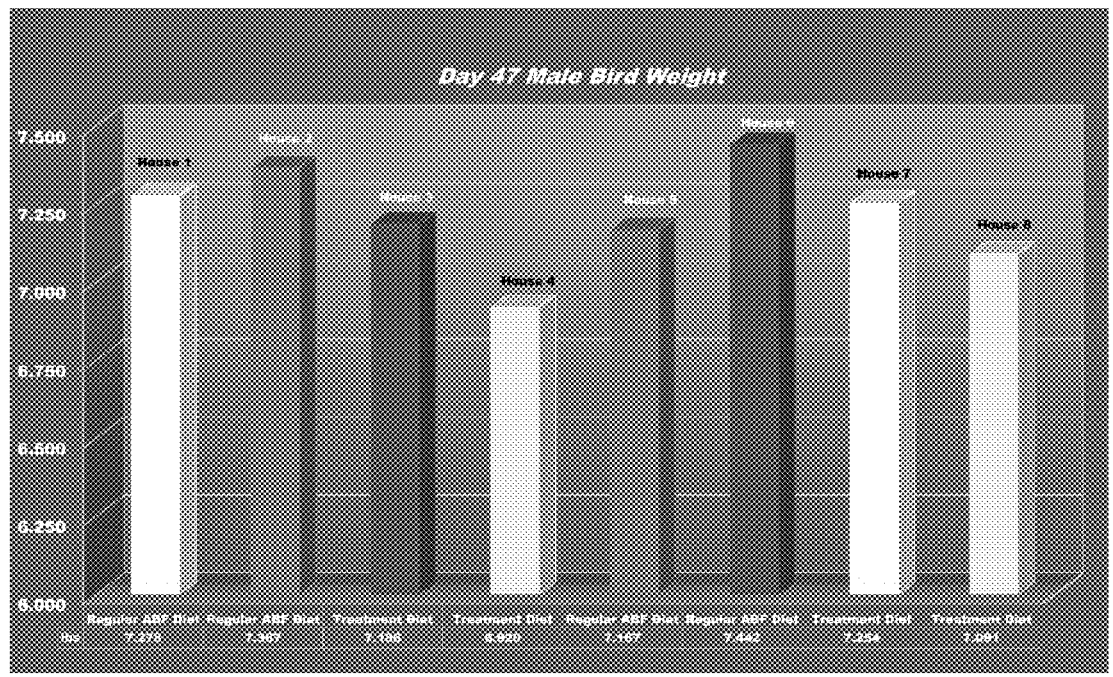
FIG. 50 is a bar graph of male bird weight (grams) measured at day 47 of the 48-day trial for different houses wherein either a regular ABF diet or a treatment embodiment as disclosed herein was used.
Figure 51:
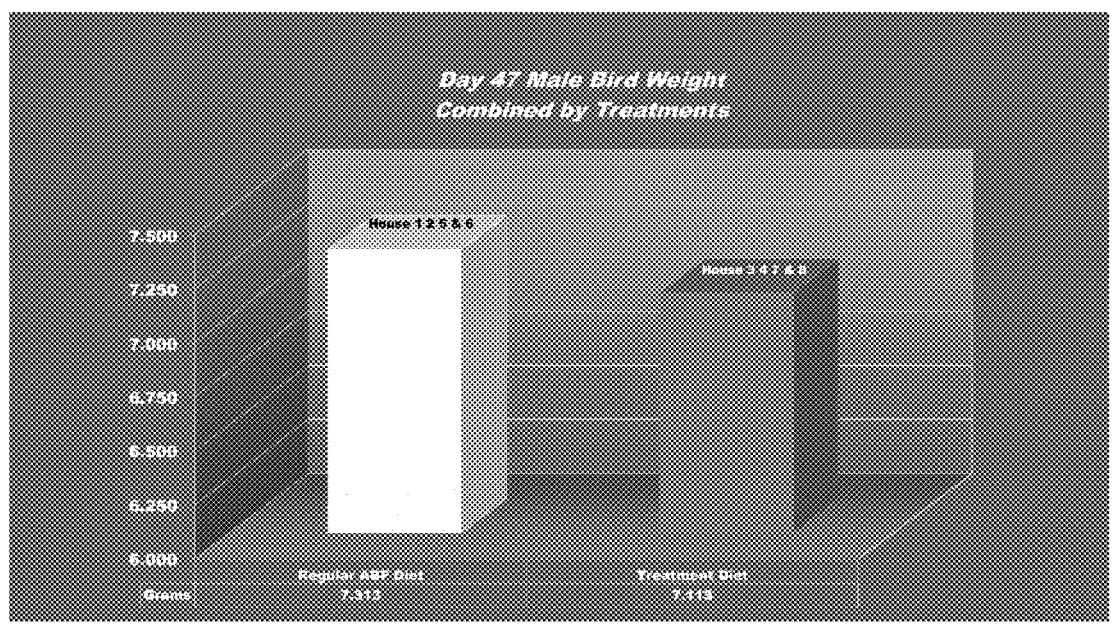
FIG. 51 is a bar graph illustrating male bird weight (grams) measured at day 47 of the 48-day trial with the measurements based on the type of treatment used (regular ABF diet versus a treatment embodiment disclosed herein).
Figure 52:
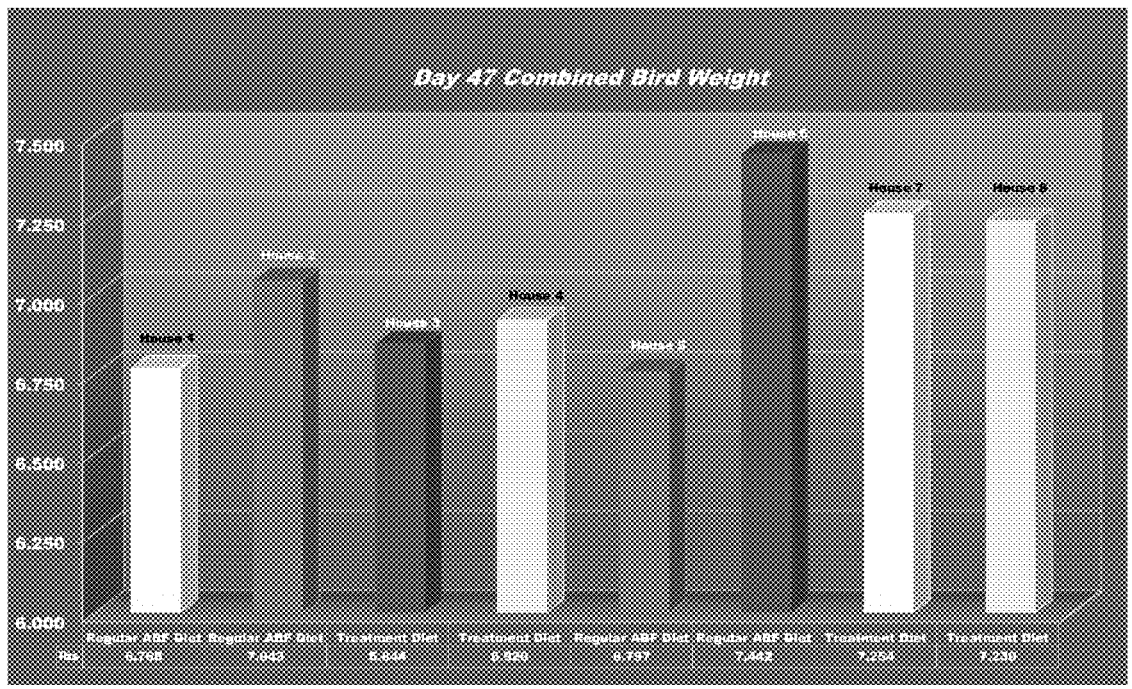
FIG. 52 is a bar graph of combined male and female bird weights (grams) measured at day 47 of the 48-day trial for different houses wherein either a regular ABF diet or a treatment embodiment as disclosed herein was used.
Figure 53:
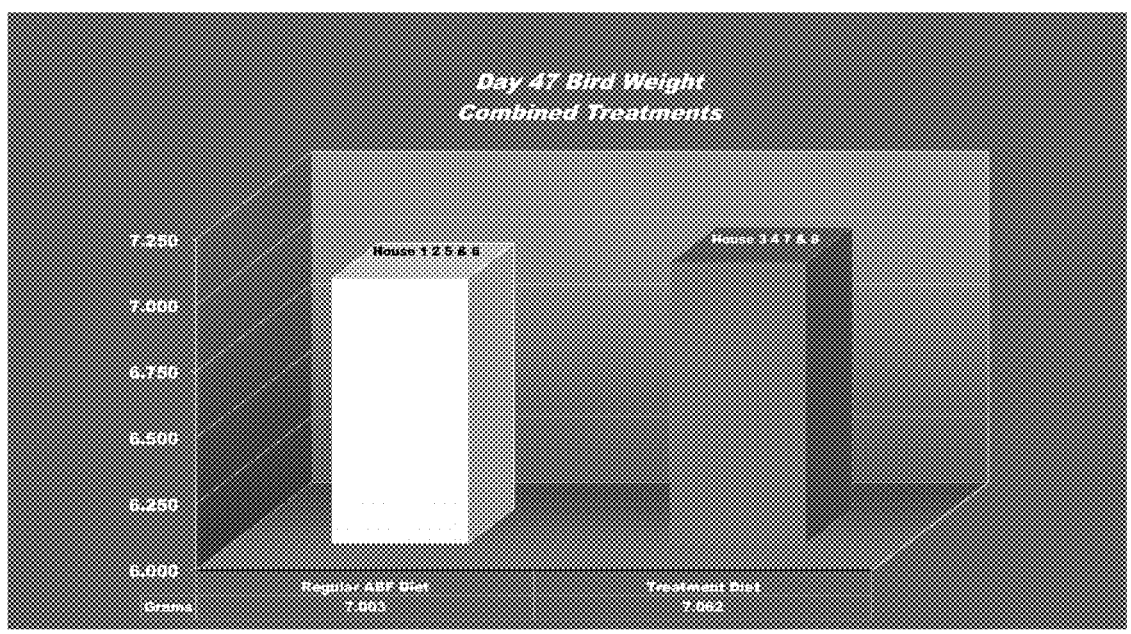
FIG. 53 is a bar graph illustrating combined male and female bird weights (grams) measured at day 47 of the 48-day trial with the measurements based on the type of treatment used (regular ABF diet versus a treatment embodiment disclosed herein).
Figure 54:
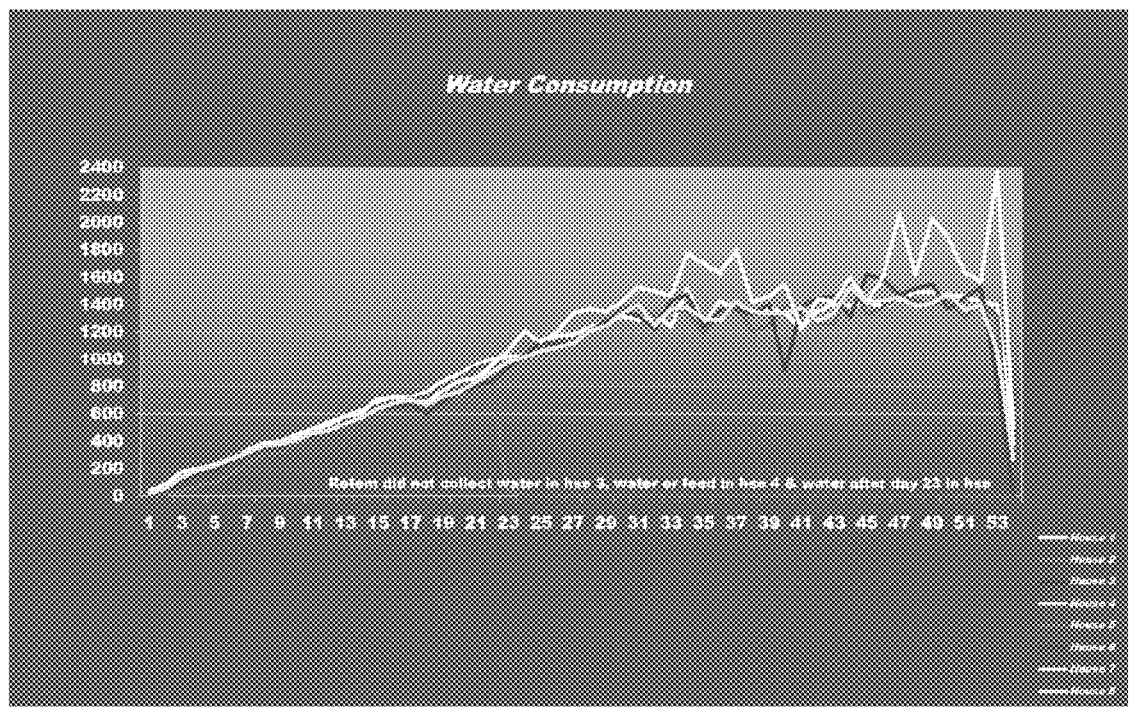
FIG. 54 is a graph (water consumption versus time [days]) illustrating results obtained from analyzing animal water consumption data.
Figure 55:
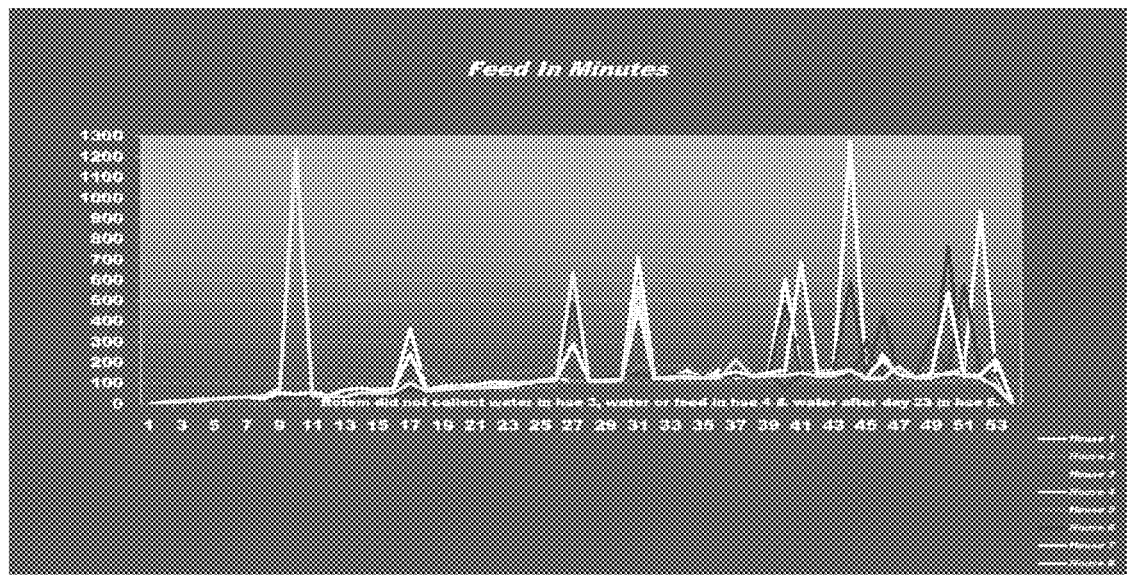
FIG. 55 is a graph (feed consumption versus time [days]) illustrating results obtained from analyzing animal feed data.
Figure 56:
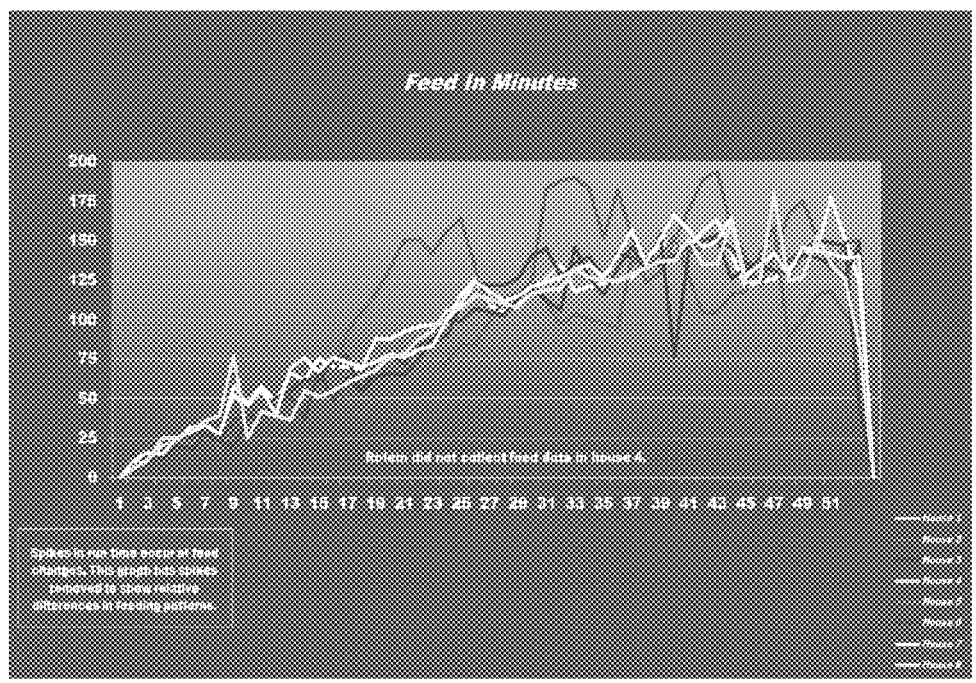
FIG. 56 is a graph (feed consumption versus time [days]) illustrating results obtained from analyzing animal feed data, with data spikes, caused at feed change times, removed to allow for analysis of relative feeding patterns.
Figure 57:
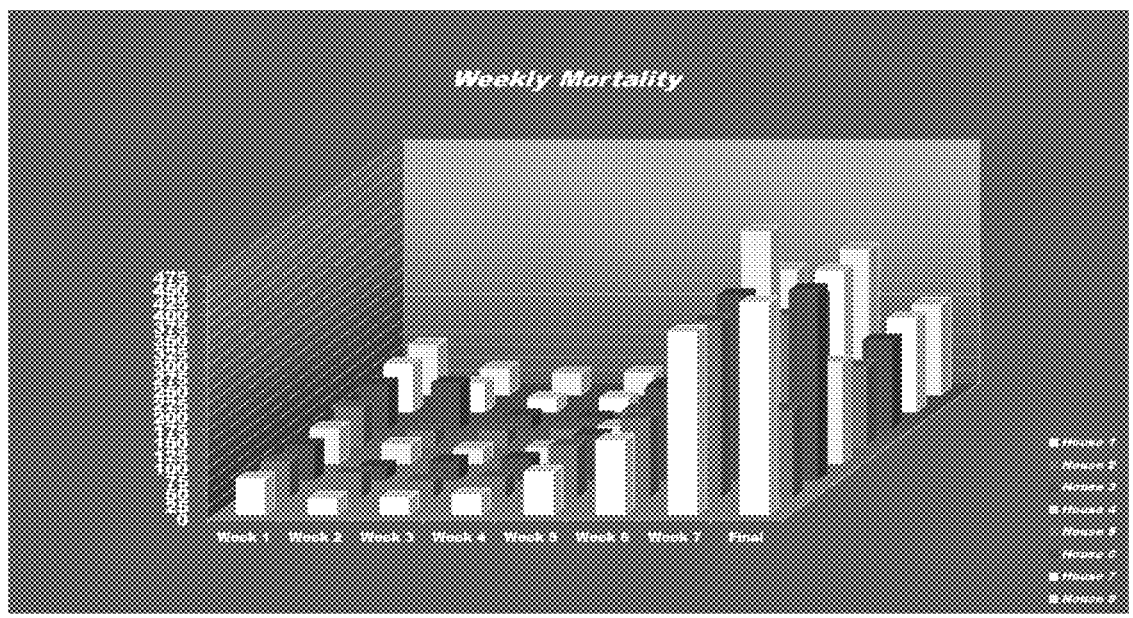
FIG. 57 is a graph (weekly mortality versus time [week] versus house) illustrating results obtained from analyzing the mortality rates in each week.

This disclosure concerns embodiments of a combination comprising *Quillaja saponaria* and *Yucca schidigera*, and *Bacillus coagulans*, and a method of administering the combination to an animal. Administration of the combination improves, i.e. lowers, the feed conversion rate in the animal.

I. DEFINITIONS

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is recited.

Administering: Administration by any route to a subject. As used herein, administration typically but not necessarily refers to oral administration.

Animal: This term can include, but is not limited to, companion animals, utility animals, and feed animals. In some embodiments, an animal can be a companion animal species that is kept as a pet, or an animal species that is raised for human consumption. Exemplary animals include, but are not limited to, vertebrates, mollusks, insects and crustaceans. Specific examples are provided herein.

Binding agent or binder: A material or substance that is used to hold or draw together other materials to form a cohesive unit. Examples include, but are not limited to, acacia, alginic acid, carboxymethylcellulose, sodium compressible sugar, ethylcellulose gelatin, liquid glucose, methylcellulose, povidone or pregelatinized starch.

Co-administration: Administering two or more agents simultaneously or sequentially in any order to a subject to provide overlapping periods of time in which the subject is experiencing effects, beneficial and/or deleterious, from each agent. One or both of the agents may be a therapeutic agent. The agents may be combined into a single composition or dosage form, or they may be administered as separate agents either simultaneously or sequentially in any order. When administered sequentially, the two or more agents are administered within an effective period of time to provide overlapping periods of time in which the subject experiences effects from each agent.

Combination: A combination comprises two or more components that are administered such that the effective time period of the first component overlaps with the effective time period of the second and subsequent components. A combination may be a composition comprising the components, or it may be two or more individual components administered substantially simultaneously, or sequentially in any order.

Companion Animal: A domesticated animal that is kept as a companion or pet.

Excipient or carrier: A physiologically inert substance that is used as an additive in a pharmaceutical composition. As used herein, an excipient or carrier may be incorporated within particles of a composition, or it may be physically mixed with particles of a composition. An excipient or carrier can be used, for example, to dilute an active agent and/or to modify properties of a composition. Examples of excipients and carriers include but are not limited to calcium carbonate, polyvinylpyrrolidone (PVP), tocopheryl polyethylene glycol 1000 succinate (also known as vitamin E TPGS, or TPGS), dipalmitoyl phosphatidyl choline (DPPC), trehalose, sodium bicarbonate, glycine, sodium citrate, and lactose.

Feed Animal: An animal that is raised for human consumption.

Feed conversion rate: A measure of an animal's efficiency in converting feed mass into increased body mass. It is also known as feed conversion ratio. Animals with a low feed conversion rate are considered efficient users of feed.

Feedstuff: "Feedstuff" refers to anything that may be consumed by an animal. The term "feedstuff" encompasses solid and liquid animal feeds (e.g., a feed ration), supplements (e.g., a mineral supplement), water, and feed additive carriers (e.g., molasses).

Saponin: A class of chemical compounds, one of many secondary metabolites found in natural sources, with saponins found in particular abundance in various plant species. More specifically, they are amphipathic glycosides grouped, in terms of structure by their composition. In certain embodiments, saponin comprises of one or more hydrophilic glycoside moieties combined with a lipophilic triterpene derivative.

Utility Animal: An animal that is raised to produce a product for human use or consumption.

II. COMBINATIONS COMPRISING BACILLUS, AND YUCCA, QUILLAJA OR BOTH

Disclosed herein are embodiments of a combination of yucca or quillaja, or both, with Bacillus. Examples of yucca include, but are not limited to, Yucca aloifolia, Yucca angustissima, Yucca arkansana, Yucca baccata, Yucca baileyi, Yucca brevifolia, Yucca campestris, Yucca capensis, Yucca carnerosana, Yucca cernua, Yucca coahuilensis, Yucca constricta, Yucca decipiens, Yucca declinata, Yucca de-smetiana, Yucca elata, Yucca endlichiana, Yucca faxoniana, Yucca filamentosa, Yucca filifera, Yucca flaccida, Yucca gigantean, Yucca glauca, Yucca gloriosa, Yucca grandiflora, Yucca harrimaniae, Yucca intermedia, Yucca jaliscensis, Yucca lacandonica, Yucca linearifolia, Yucca luminosa, Yucca madrensis, Yucca mixtecana, Yucca necopina, Yucca neomexicana, Yucca pallida, Yucca periculosa, Yucca potosina, Yucca queretaroensis, Yucca reverchonii, Yucca rostrata, Yucca rupicola, Yucca schidigera, Yucca schottii, Yucca sterilis, Yucca tenuistyla, Yucca thompsoniana, Yucca treculeana, Yucca utahensis, or Yucca valida. In certain disclosed working embodiments the yucca, was Yucca schidigera.

Examples of quillaja include, but are not limited to, Quillaja brasiliensis, Quillaja lanceolata, Quillaja lancifolia, Quillaja molinae, Quillaja petiolaris, Quillaja poeppigii, Quillaja saponaria, Quillaja sellowiana, or Quillaja smegmadermos. In particular disclosed working embodiments the quillaja was Quillaja saponaria.

A person of ordinary skill in the art will appreciate that, as used herein, a plant name may refer to the plant as a whole, or to any part of the plant, such as the roots, stem or trunk, bark, leaves, flower, flower stems, or seeds or a combination thereof. These plant parts may be used fresh, or dried, and may be whole, pulverized, mashed, comminuted or ground up. Extracts from any part or parts of the plant are also contemplated, such as chemical extracts, or extracts obtained by pressing, or any other methods of concentrating or extracting oils or other extracts known to those in the art or that are hereafter discovered. Plant extracts may include compounds that are saponins, triterenoids, polyphenols, antioxidants or resveratrol. In certain embodiments, an extracts from a composition comprising Yucca schidigera and Quillaja saponaria comprises a minimum 15% total dissolved solids composed of triterpenic and steroidal saponins, resveratols, and other naturally occurring glicocomponents, polyphenols, salts and sugars.

A composition comprising yucca and/or quillaja may also include carriers and binding agents suitable to formulate the yucca and/or quillaja for administration to an animal. In certain working embodiments, this composition was a commercially available product, Nutrafito® Plus, available from Desert King International.

The combination also comprises Bacillus. Bacillus is a genus of Gram-positive, rod-shaped bacteria. Examples of Bacillus include, but are not limited to Bacillus alcalophilus Bacillus alvei, Bacillus aminovorans, Bacillus amyloliquefaciens, Bacillus aneurinolyticus, Bacillus anthracis, Bacillus aquaemaris, Bacillus atrophaeus, Bacillus boroniphilus, Bacillus brevis, Bacillus caldolyticus, Bacillus centrosporus, Bacillus cereus, Bacillus circulans, Bacillus coagulans, Bacillus firmus, Bacillus flavothermus, Bacillus fusiformis, Bacillus galliciensis, Bacillus globigii, Bacillus infernus, Bacillus larvae, Bacillus laterosporus, Bacillus lentus, Bacillus licheniformis, Bacillus megaterium, Bacillus mesentericus, Bacillus mucilaginosus, Bacillus mycoides, Bacillus natto, Bacillus pantothenticus, Bacillus polymyxa, Bacillus pseudoanthracis, Bacillus pumilus, Bacillus schlegelii, Bacillus sphaericus, Bacillus sporothermodurans, Bacillus stearothermophilus, Bacillus subtilis, Bacillus thermoglucosidasius, Bacillus thuringiensis, Bacillus vulgatis, or Bacillus weihenstephanensis. In particular disclosed working embodiments the Bacillus is Bacillus coagulans. Compound(s) obtained from the bacteria are also contemplated. Methods of obtaining compounds from bacteria are well known in the art. In some embodiments, the Bacillus comprises, consists essentially of, or consists of a Bacillus spore, such as a Bacillus coagulans spore.

A composition comprising Bacillus may also include additional materials, such as carriers or binding agents, suitable to formulate the Bacillus for administration to an animal. In certain disclosed working embodiments, a composition comprising Bacillus coagulans was Ganpro®, a commercial product available from Ganeden Biotech, Ohio. In other disclosed working embodiments, a composition comprising Bacillus coagulans was Provia 6086®, available from Prince Agri Products, Inc.

Disclosed exemplary embodiments concern a combination comprising a composition of Bacillus, and a composition comprising, or consisting essentially of, yucca, quillaja, or both. In some examples, the composition consists of yucca and quillaja. In some embodiments the combination is a composition comprising Bacillus and yucca, quillaja, or both. Alternatively, the combination may be a composition consisting essentially of Bacillus and yucca, quillaja, or both, or it may be a composition consisting of Bacillus, yucca and quillaja.

In some embodiments, the combination was admixed with a feedstuff. In certain embodiments the combination is formulated to be suitable to form a homogeneous mixture with the feedstuff, such as by crushing, crumbling, grinding or otherwise sizing the combination. Alternatively, the combination may be formulated as a solution, suspension or slurry. In embodiments where the combination comprises two or more compositions, the compositions may be formulated separately or substantially together. The compositions may also be admixed with the feedstuff sequentially, in any order, or substantially simultaneously.

The components of the combination are selected to contain selected amounts of *Bacillus, yucca* and/or *quillaja*. In certain embodiments, these amounts are effective to provide a beneficial feed conversion enhancement in animals. For example, for poultry, the amount of *Bacillus coagulans*, administered in certain working embodiments as Ganpro®, is from about 0.5 to 2.5 grams per head per day, preferably about 1 gram per head per day; for cattle, the range is from about 10 to about 50 grams per head per day, preferably from about 28 to 36 grams per head per day; and for swine the range is from about 2 to about 10 grams per head per day, preferably about 5.5 grams per head per day. In particular working examples, the *Bacillus coagulans* was admixed with feedstuff at about 7.5 grams per ton (2000 pounds) of feedstuff. In other embodiments, the amount of *Bacillus coagulans*, administered in certain embodiments as Ganpro® or Provia 6086®, is from about 0.5 grams to less than 7.5 grams per ton, such as from 2 grams to 7.25 grams per ton, or from 5 grams to 7 grams per ton. In other examples, the amount of *Bacillus coagulans*, administered in certain embodiments as Ganpro® or Provia 6086®, is from greater than 7.5 grams to greater than 10 grams per ton, such as from greater than 7.5 grams per ton to 10 grams per ton, or from 7.75 grams per ton to 8 grams per ton.

In some embodiments the amount of *yucca* administered to an animal is from about 0 to greater than about 10 ounces per ton of feedstuff, preferably from about 1 to about 5 ounces. In other embodiments the amount of *quillaja* administered to an animal is from about 0 to greater than about 10 ounces per ton of feedstuff, preferably from about 1 to about 5 ounces. In certain embodiments, both *yucca* and *quillaja* are administered, and the combined amount administered is from greater than 0 to greater than about 10 ounces per ton of feedstuff, preferably from about 2 to about 6 ounces. In other embodiments, a composition comprising *yucca* and *quillaja* is administered at from greater than 0 ppm to about 500 ppm, such as from about 50 ppm to about 400 ppm, or from about 100 ppm to about 300 ppm. In certain embodiments, a composition comprising *yucca* and *quillaja* is administered at from greater than 0 ppm to less than 125 ppm, such as from greater than 0 ppm to 124 ppm or from greater than 0 ppm to 100 ppm. In other embodiments, a composition comprising *yucca* and *quillaja* is administered at from greater than 125 ppm to 500 ppm, such as from about 126 ppm to 400 ppm, or from 150 ppm to 300 ppm. In certain preferred embodiments, *Yucca schidigera* and *Quillaja saponaria* were administered to avians as Nutrafito® Plus, at from about 2 to about 6 ounces per ton of feedstuff. In working embodiments, Nutrafito® Plus was administered to avians at about 125 ppm (parts per million) or at about 4 ounces per ton of feedstuff.

In some embodiments, the animals are not fed 125 ppm Nutrafito® Plus. In other embodiments, the animals are not fed 7.5 g per ton of Ganpro® or Provia 6086®. In certain embodiments, the animals are not fed 125 ppm Nutrafito® Plus and 7.5 g per ton of Ganpro® or Provia 6086®. In certain embodiments, these animals are avians, and in particular embodiments, these animals are chickens.

In some embodiments, the animals are not fed 125 ppm of a composition comprising *Yucca schidigera* and *Quillaja saponaria*. In other embodiments, the animals are not fed 7.5 grams per ton of a composition comprising *Bacillus coagulans*.

In certain embodiments, the animals are not fed 125 ppm of a composition comprising *Yucca schidigera* and *Quillaja saponaria* and 7.5 grams per ton of a composition comprising *Bacillus coagulans*. In certain embodiments, these animals are avians, and in particular embodiments, these animals are chickens.

In some embodiments the combination and/or compositions further comprise any additional material beneficial to the recipient and or facilitate formulations, such as a vitamin, an antibiotic, a trace mineral, a bulking agent, a carrier, a vaccine, a colorant, a taste enhancer, corn, soybean meal, corn oil, limestone, salt, distillers dried grains with solubles (DDGS), dicalcium phosphate, sodium sesquicarbonate, methionine source, lysine source, L-threonine, choline, or any combination thereof.

III. METHODS AND BENEFITS OF USING THE COMBINATION

The combination or composition may be administered to an animal. The animal may be a vertebrate, mollusk, insect or crustacean. Exemplary vertebrates include, but are not limited to, avians, mammals, amphibians, reptiles and fish. In certain embodiments, the animal is not an avian. In certain examples, the non-avian animal is a mammal, fish, reptile, amphibian, insect, crustacean or mollusk. The combination or composition may be used for aquaculture, such as in the farming of fish, crustaceans, mollusks and other aquatic organisms. Farmed fish include, but are not limited to, salmon, trout, tilapia, bass, sea bass, bream, carp, catfish, mullet, grouper, or amberjack. The combination or composition may also be administered to a companion animal or ornamental fish, such as a goldfish, koi or other pond, tropical or aquarium fish. In some embodiments, the animal is a warm blooded animal, such as a mammal or an avian. In particular embodiments, the animal is an avian, including, but not limited to, chicken, turkey, goose, duck, Cornish game hen, quail, pheasant, guinea-fowl, ostrich, emu, swan or pigeon. In some other embodiments, the animal is a feed animal such as a livestock animal, or a utility animal. Exemplary feed and utility animals include, but are not limited to, ruminant animals such as a bovine, sheep, goat, deer, bison, buffalo, elk, llama, alpaca, antelope or camel; non-ruminant animals such as swine, horses, or donkeys; poultry species such as chickens, ducks, geese, turkeys, quail, guinea fowl or pigeon; or other feed animals such as fish, crustaceans, reptiles and amphibians.

In some embodiments, the animal is a companion animal. Exemplary companion animals include, but are not limited to: canines; felines; rabbits; rodents, such as a rat, mouse, hamster, gerbil, guinea pig or chinchilla; birds, such as parrots, canaries, parakeets, finches, cockatoos, macaws, parakeets or cockatiel; reptiles, such as snakes, lizards, tortoises or turtles; fish; crustaceans; and amphibians, such as frogs, toads and newts.

In some embodiments, administration of a combination or composition comprising a *Bacillus* species with *yucca*, *quillaja*, or both enhances the feed conversion rate in animals, relative to animals fed a standard diet, or a diet with only *Bacillus* or only *yucca* and/or *quillaja* added.

A feed conversion rate, also known as feed conversion ratio, is a measure of an animal's efficiency in converting feed mass into increased body mass. Animals with a low feed conversion rate are considered efficient, as they require less feed to reach a desired weight. Feed conversion rates vary from species-to-species. For example, for pigs a typical feed conversion rate is about 3.0-3.2; for poultry a typical rate is about 2; and for cattle the feed conversion rate can vary from about 5 to about 20.

In some embodiments, the feed conversion rate was enhanced by about 0.5% to greater than 20%, preferably by about 2% to about 10%, and in certain working embodiments, by about 3% to about 5%. Certain working embodiments disclosed herein describe a feed conversion rate enhancement for broiler meat-type chickens of about 4-5%. The combination or composition of Bacillus with yucca, quillaja, or both, is fed to the animals during any stage of their lifecycle in which they are consuming food. The combination or composition of Bacillus with yucca, quillaja, or both may be fed to the animal starting from any time from birth, weaning or hatching, and finishing at any time prior to death. The animal may be fed the combination or combination once a day or 2, 3, 4 or more times a day. Alternatively, the combination may be available continuously to the animal. In some embodiments, the combination is included in a milk replacer or similar feed or supplement for a newly born or pre-weaning animal. In certain embodiments where the animals are avians, the combination is fed after hatching, or at any stage thereafter. In certain working embodiments, the combination was admixed with feedstuff and fed to 1 day old broiler chickens, and thereafter until harvest, at about 8 weeks. The amount of the admixed feedstuff provided to the chickens was varied according to their needs as they grew in size.

In some embodiments, the combination or composition of the quillaja and/or yucca with the Bacillus, has a beneficial effect on animal health, typically, a beneficial effect on the digestive system, including the stomach and intestines. Certain embodiments have a beneficial effect on villi length.

IV. WORKING EXAMPLES

The subject matter disclosed herein is further understood by reference to the following examples, which are intended to be purely exemplary of the present disclosure. The present disclosure is not limited in scope by the exemplified embodiments, which are intended as illustrations of single aspects of the claimed invention only. Any methods that are functionally equivalent are within the scope of the claimed invention. Various modifications of the presently disclosed subject matter, in addition to those described herein, will become apparent to those skilled in the art from the foregoing description and accompanying figures. Such modifications fall within the scope of the appended claims.

Example 1

96 pens were randomly filled with 20 male R×Ross 708 broiler chicks. The chicks were fed one of six diets: 1) a positive control (PC) diet consisting of a Standard OK Foods Diet without saponins; 2) a negative control (NC) diet consisting of the PC diet without any direct-fed microbial (DFM); 3) a PC diet with added Nutrafito® Plus; 4) a NC diet with Nutrafito® Plus; 5) a NC diet with added Ganpro®; and 6) a NC diet with added Nutrafito® Plus and Ganpro®. Nutrafito® Plus was added at an inclusion rate of 125 ppm, or 0.25 pounds per ton of feed. The inclusion rate of Ganpro® was 7.5 grams per ton of feed. Feed was fed on a per pound basis as follows:

Starter—1.5 pounds per bird; Grower—3.0 pounds per bird; Finisher 1—4.0 pounds per bird; Finisher 2—To market. The birds were weighed on days 0, 7, 14, 28, 42 and 48, the end of the trial.

TABLE 1

Results from trial of Nutrafito Plus ® and Ganpro ® combination

| Treatment | Positive Control | Negative Control | PC + Nutrafito ® Plus | NC + Nutrafito ® Plus | NC + Ganpro ® | NC + Nutrafito ® Plus + Ganpro ® |
|---|---|---|---|---|---|---|
| Birds Placed | 320 | 320 | 320 | 320 | 320 | 320 |
| Birds Processed | 293 | 292 | 298 | 288 | 295 | 293 |
| Total Mortality | 8.44% | 8.75% | 6.88% | 10.00% | 7.81% | 8.44% |
| Pounds Processed | 2,444.105 | 2,459.663 | 2,481.341 | 2,415.285 | 2,470.210 | 2437.02 |
| Average Weight | 8.347 | 8.426 | 8.332 | 8.394 | 8.380 | 8.319 |
| Feed Consumed | 4,572.530 | 4,481.910 | 4,542.530 | 4,461.865 | 4,545.865 | 4389.96 |
| Feed Conversion$^{-1}$ | 1.871 | 1.822 | 1.831 | 1.847 | 1.840 | 1.801 |
| Feed Conversion$^{-2}$ | 1.789 | 1.760 | 1.778 | 1.773 | 1.779 | 1.740 |
| Feed Conversion$^{-3}$ | 1.813 | 1.751 | 1.775 | 1.782 | 1.777 | 1.748 |
| Feed Conversion$^{-4}$ | 1.732 | 1.689 | 1.723 | 1.707 | 1.716 | 1.686 |
| Growth Rate | 17.390 | 17.553 | 17.359 | 17.487 | 17.458 | 17.331 |

[1] Feed conversion BC = pounds of feed/pounds of live weight delivered to plant not including mortality and culls.
[2] Feed conversion MCA = feed conversion with mortality and cull weight adjustment. Pounds feed/pounds of live weight and weight of all mortality and cull birds.
[3] Adjusted conversion B/C = feed conversion B/C adjusted to 6 pounds body weight using .06 pounds = .01 point of feed conversion.
[4] Adjusted conversion MCA = feed conversion MCA adjusted to 6 pounds body weight using .06 pounds = .01 point of feed conversion.

Results: Table 1 and FIGS. 1-22 show the results from the trial. As can be seen in in Table 1, and in FIGS. 5-12 and 19-20, the combination of Nutrafito® Plus and Ganpro® significantly reduced, by about 3-4%, the feed conversion rate by day 48, relative to both the controls and to the chickens given only feed with Nutrafito® Plus or only feed with Ganpro®.

Example 2

Study Animals: Hub×Cobb500 Broiler Chickens from O.K. Farms, Inc., Stigler Hatchery, Stigler, Ok. Males and females (straight run as hatched), with initial weight 35-60 grams.

Treatment

| | |
|---|---|
| 1 | ABF Control Diets |
| 2 | ABF Control Diets |
| 3 | Treatment Diets |

| | |
|---|---|
| 4 | Treatment Diets |
| 5 | ABF Control Diets |
| 6 | ABF Control Diets |
| 7 | Treatment Diets |
| 8 | Treatment Diets |

The treatments diets (FIG. 23) included a combination of Nutrafito® Plus and a composition comprising *Bacillus coagulans* (Ganpro® and/or Provia 6086®). Nutrafito® Plus was added at an inclusion rate of 125 ppm, or 0.25 pounds per ton of feed. The inclusion rate of the *Bacillus coagulans* composition was 7.5 grams per ton of feed.

Study Design:

Housing:

Eight (8) commercial broiler houses similar in construction, design, size, compass direction, insulation, heating, ventilation, lighting, watering system, and feed equipment were used for the study. The number of birds placed per house and general house environment were similar as possible so that differences in performance due to housing were minimized.

Feeder Space:

Two lines of Cumberland Hi Lo pan feeders were providing feed for a minimum of 64 birds per pan throughout the study. Additional ChickMate pan feeders provided additional feeder space during the brooding period.

The Floor space:

Stocking density was 0.86 sq ft/bird.

Feed and Water:

Feed and water was provided ad libitum consumption.

Environment:

Each house has insulated, solid sidewalls with insulated endwalls, and ceiling. The minimum ventilation system provides slight negative pressure with two, 36" fans mounted on the endwalls of the house. Tunnel ventilation uses eight 48" fans mounted in the end of the house. A computerized controller using 7 sensors placed throughout the house controls the house temperature.

Vaccinations:

The birds received Marek's, IBD and NC/IBV vaccine at the hatchery. LT vaccine was administered at the hatchery.

Basal Diet:

Diets were a typical commercial starter, grower, finisher 1 and finisher 2 used by O.K. Farms. The only differences in the diets were as indicated in Treatments. All diets were pelleted. The starter diet was crumbled after pelleting. Grower & finisher feeds were also crumbled.

Procedure:

Feed Preparation:

Feed for the trial was made and delivered under the supervision of the Technical Services Department. Samples were taken from the truck prior to delivery to the bins on the farm. Samples were retained until the study was complete. Feed was fed on a pound per bird placed basis as follows:

Starter—1.5 pounds per bird placed;
Grower—3.00 pounds per bird placed;
Finisher One—4.00 pounds per bird placed;
Finisher Two—As needed to market.

Bird Placement:

The eight houses on the farm were filled with 15,300 day-old broiler chicks from HubbxCobb500 breeder flocks. Chicks from each breeder flock were equally distributed in each house. An investigator was stationed at the hatchery to confirm the distribution of each breeder flock. Chick boxes were labeled by house before they were loaded on the delivery truck. The label on each chick box was verified and the total number of boxes for each house was verified before it was unloaded in the house and recorded. They were placed at 0.86 sq. ft./bird.

Randomization:

Technical Services provided the randomization procedure for assigning the color-coded treatments to four houses according to an allotment of treatment to houses. Houses were identified with study number, house number, and treatment color code as follow: House #1—White, House #2—Orange, House #3—Green, House #4 Yellow, House #5—Orange, House #6—Green, House #7—White, House #8—Yellow.

Observations:

The broiler house caretaker observed the birds in all houses daily. In addition, the Investigator was examining each house at least 3 days per week to look for clinical signs of disease and to assess the environment and litter condition.

Mortality:

Mortality and culling records were average for the week these birds were processed.

Final Bird Weights:

At the end of the grow-out period birds were processed. The gross and tare weights of the trucks used to transport the birds from each house to the processing facility was determined and recorded. Likewise the number of birds placed on the trucks at the grow-out facility was recorded. Authenticated copies of these records were placed in the study file as raw data.

Processing:

At the end of the grow-out period, birds were processed at O.K. Farms, Inc. Processing Plant, North 6th and Reed, Fort Smith, Ariz. 72902 (Establishment number P-165S). A USDA Certificate of Condemnation was prepared and copies were collected as a raw data for each house separately.

Disposal of Unused Feed:

Any unused or weigh back feed was recorded and documented when it was returned to the mill.

Raw Data:

All original raw data were assembled as a part of the Investigator's report and forwarded to the sponsor upon completion of the study. A readable, exact, dated copy of the data were retained in a file and stored in a secured area by OK Foods, Inc.

Completed Data:

The results of the performance data are enclosed in tabular (Table 2) and graphic form (FIGS. 24-57). As can be seen in Table 2, the feed conversion rates are improved for the animals that had the combination of Nutrafito® Plus and the *Bacillus coagulans* composition administered with the feed, relative to the animals that only received the feed.

TABLE 2

| | House 1, 2, 5, 6 Regular ABF Diet | House 3, 4, 7, 8 Treatment Diet |
|---|---|---|
| Birds Placed | 61,200 | 61,200 |
| Birds Processed | 57,305 | 56,979 |
| 7-Day Mortality | 0.50% | 0.53% |
| 14-Day Mortality | 0.82% | 0.81% |
| Total Mortality | 6.37% | 6.90% |
| Pounds Processed | 417,200 | 415,640 |
| Average Weight | 7.280 | 7.294 |
| Feed Consumed | 902,945 | 896,995 |
| Feed Conversion$^{-1}$ | 2.164 | 2.158 |
| Feed Conversion$^{-2}$ | 2.090 | 2.081 |

TABLE 2-continued

|  | House 1, 2, 5, 6 Regular ABF Diet | House 3, 4, 7, 8 Treatment Diet |
| --- | --- | --- |
| Feed Conversion[3] | 2.118 | 2.109 |
| Feed Conversion[4] | 2.043 | 2.032 |
| Growth Rate | 13.482 | 13.508 |
| Percent Condemn | 0.45% | 0.41% |

[1] Feed conversion BC = pounds of feed/pounds of live weight delivered to plant not including mortality and culls.
[2] Feed conversion MCA = feed conversion with mortality and cull weight adjustment. Pounds feed/pounds of live weight and weight of all mortality and cull birds.
[3] Adjusted conversion B/C = feed conversion B/C adjusted to 7.00 pounds body weight using .06 pounds = .01 point of feed conversion.
[4] Adjusted conversion MCA = feed conversion MCA adjusted to 7.00 pounds body weight using .06 pounds = .01 point of feed conversion.

Example 3

Study Animals:

Forty-eight female rats ordered from Charles River Labs were randomly assigned to two rats per cage. Three cages were randomly assigned to each treatment. Rats were allowed ad libitum access to powdered Teklad 2014 prior to initiation of the study. Rats weighed approximately 180 g at the start of the experiment.

Environmental Conditions:

Temperature was set to 68° F. and lighting to 12 hours light:12 hours dark. Bedding was changed as needed throughout the study. Actual temperature ranged from 69.4° F. to 75.4° F. Humidity ranged from 31% to 73%.

Treatment:

On day 1 of the study, old feed from feeders was replaced with freshly-prepared diets. Rats were weighed on the first day of the trial, after 14 days on feed, after 21 days on feed and before sacrifice at day 28.

The control diet was Teklad 2014. Treatment diets were prepared with inclusion of supplement in Teklad 2014. The treatments diets included *Bacillus coagulans* (Provia 6086®), Nutrifito® Plus, *Yucca* extract, *Quillaja* extract, a combination of Provia 6086® and Nutrafito® Plus, a combination of Provia 6086® and *Yucca* and a combination of Provia 6086® and *Quillaja*. The inclusion rate of the Provia 6086 was 0.000825%, Nutrifito® Plus was 0.0125%, *Yucca* was 0.0125% and *Quillaja*: was 0.0125%. Treatment duration was 28 days.

Plasma Purification:

Whole blood was subjected to centrifugation (5000×g) for 20 minutes. Plasma was aliquoted into 0.500 mL volumes and stored at −80° C. until analysis.

Plasma Cytokine Analysis:

Plasma from all groups was analyzed for Interleukin-6 (IL-6; Cat No. MBS012805, MyBioSource) and Interleukin-10 (IL-10, Cat No. MBS034393, MyBioSource).

Statistical Analysis of ELISA Data:

Data gathered from ELISA was interpolated via standard curve using Graphpad Prism 6.0. Subsequent data was evaluated for normality and then analyzed by two-way ANOVA to determine effect of diet supplementation. Post-hoc tests were used to determine differences between groups.

Figure 58:
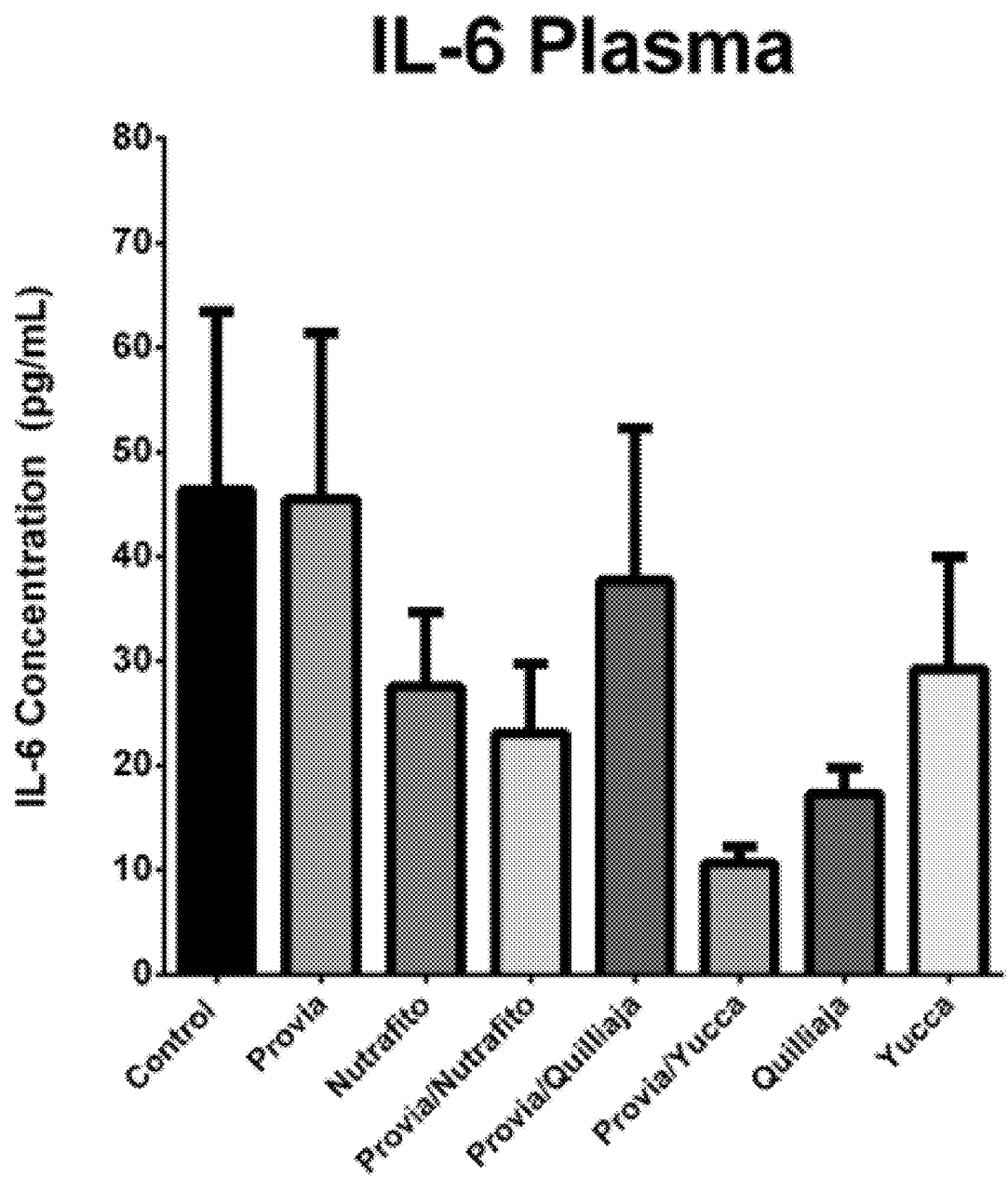
FIG. 58 is a graph of IL-6 concentration versus treatment illustrating the concentration of IL-6 in rat plasma after 28 days of inclusion of each supplement in the diet.
Figure 59:
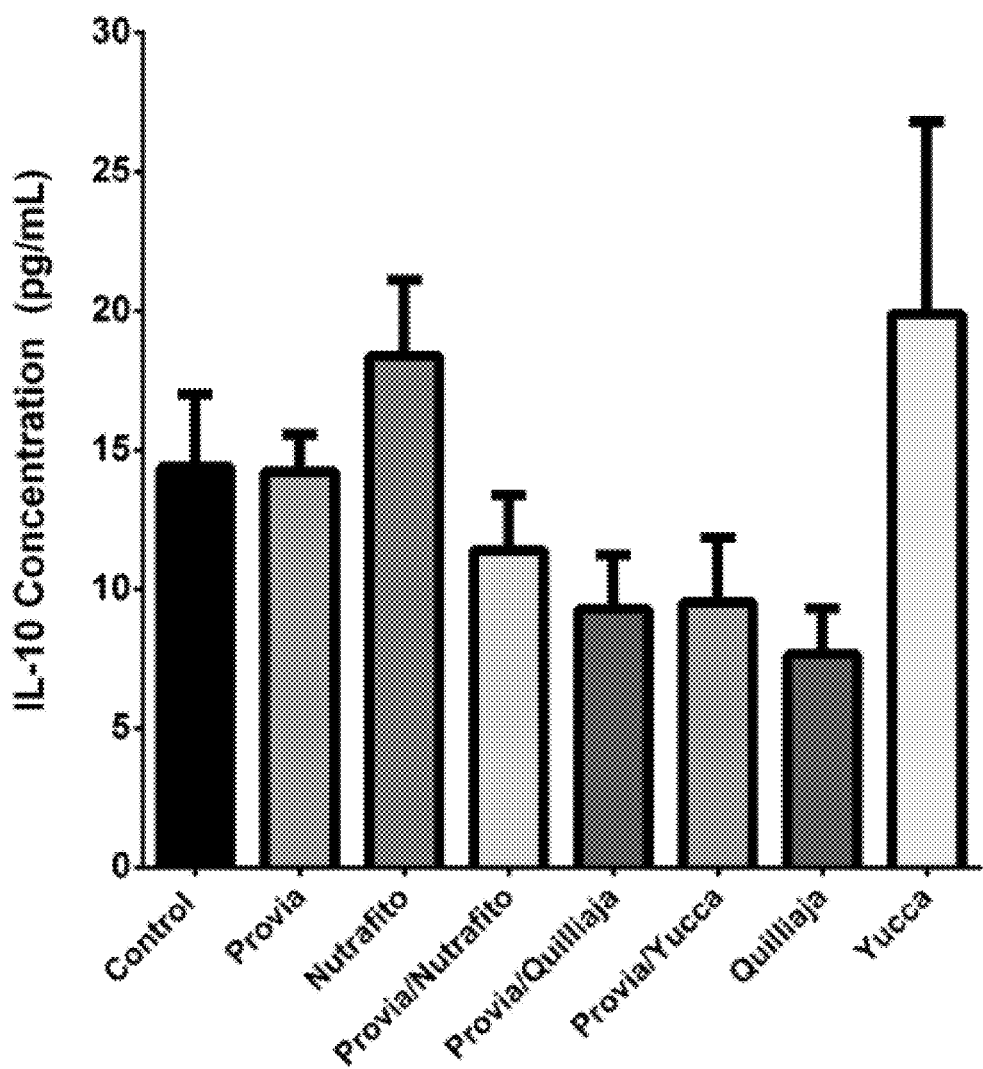
FIG. 59 is a graph of IL-10 concentration versus treatment illustrating the concentration of IL-6 in rat plasma after 28 days of inclusion of each supplement in the diet.

Completed Data:

The concentration of IL-6 and IL-10 in the plasma of rats was determined in this project to evaluate the effect of treatment on immune system function. The results of the data are included in graphic form (FIGS. 58-59). As can be seen in FIG. 58, Nutrifito® Plus, *Yucca* extract, the combination of Provia 6086® and Nutrafito® Plus and the combination of Provia 6086® and *Yucca* extract resulted in a lower plasma concentration of IL-6 when compared to control after 28 days of inclusion in the diet. As can be seen in FIG. 59, *Quillaja*, the combination of Provia 6086® and Nutrifito® Plus, the combination of Provia 6086® and *Yucca* extract and the combination of Provia 6086® and *Quillaja* resulted in a low plasma concentration of IL-10 when compared to control after 28 days of inclusion in the diet. These results indicate that inclusion of these supplements will alter the production of cytokines that regulate homeostasis and possibly physiological inflammation. IL-6 is generally considered a pro-inflammatory cytokine and IL-10 is generally considered an anti-inflammatory cytokine. Both of these cytokines are considered myokines, or factors produced by muscle tissue during tissue recovery. Thus, these data indicate that the supplements regulate gut-influenced cytokine production and potentially muscle growth through cytokine suppression. This regulation will result in less energy expenditure to cytokine production, improved nutrient uptake and nutrient utilization. Taken in combination with the improved feed conversion and weight gain observed in poultry projects described in this application, these data indicate that one biological action of these supplements is to improve nutrient uptake through alteration of gut enterocyte function and production of cytokines in the lamina propria and connective tissue of the gastrointestinal tract. Similarly, alteration of the production of myokines can lead to enhanced muscle growth leading to increased weight gain as less energy is expended on the differentiation and proliferation of myosatellite cells versus the increase in size of muscle filaments.

Example 4

In a comparison test, two groups of turkeys, were administered a base diet or a base diet supplemented with a combination of Nutrafito® Plus and Provia 6086® for the first 12 weeks of life. The birds were in pens for 21 days at 1.1 sq. ft./bird. Each group was then split into 10 pens, at 3.75 sq. ft./bird. The weights of the birds were recorded at the start and after 141 days, and the average daily weight gain (ADG) was calculated (Table 3). A feed conversion ratio was calculated from the Total Pounds of Feed/Net Pounds of bird. The feed cost per live pound of bird was calculated from the Total cost of the Feed/Net pounds of bird. After factoring in other costs, a Total Cost per Live Pound of Bird (Total Live) was calculated for each group (Table 3).

TABLE 3

|  | Integrator Current Diet | Nutrafito Plus ®/ Provia 6086 ® |
| --- | --- | --- |
| Total Head | 400 | 400 |
| Net Weight | 46.05 | 46.53 |
| ADG | 0.3266 | 0.3300 |
| Net Pounds | 18,420 | 18,612 |
| Yield Test Weight | 46.05 | 46.53 |
| Feed Conversion | 2.27 | 2.24 |
| Total Feed Cost | 6,969 | 6,921 |
| Total Feed Pounds | 41,813 | 41,691 |
| Feed Cost Per Ton | $333 | $332 |
| Feed Conversion | 2.27 | 2.24 |
| Feed Cost Live LB | $0.378 | $0.372 |
| All Other Cost Live | $0.173 | $0.171 |
| Total Live | $0.551 | $0.543 |

Figure 60:
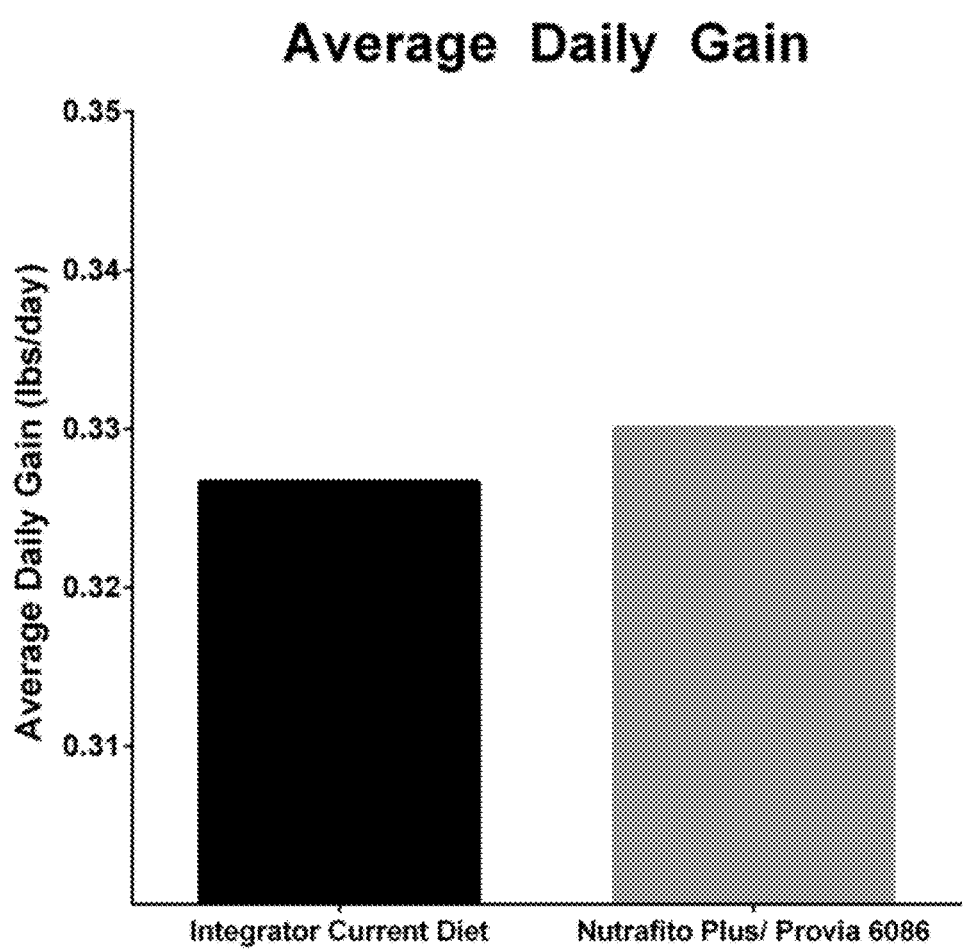
FIG. 60 is a graph of average daily gain (ADG) versus treatment illustrating the effect of the combination on the ADG of turkeys.
Figure 61:
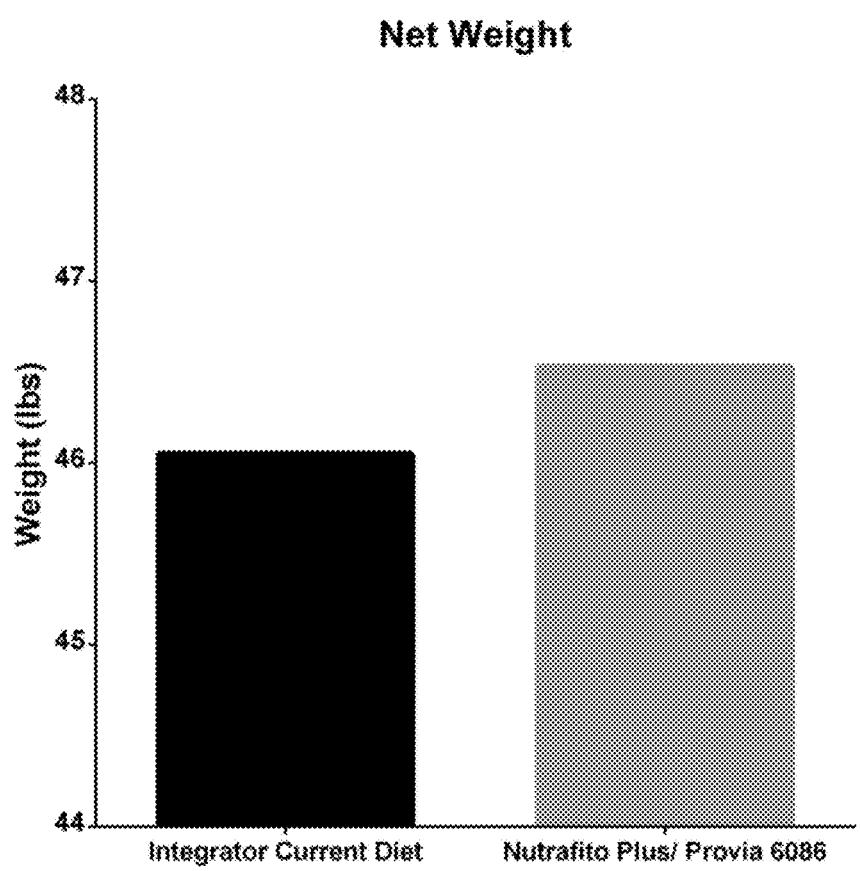
FIG. 61 is a graph of weight versus treatment, illustrating the effect of the combination on the net weight of turkeys.
Figure 62:
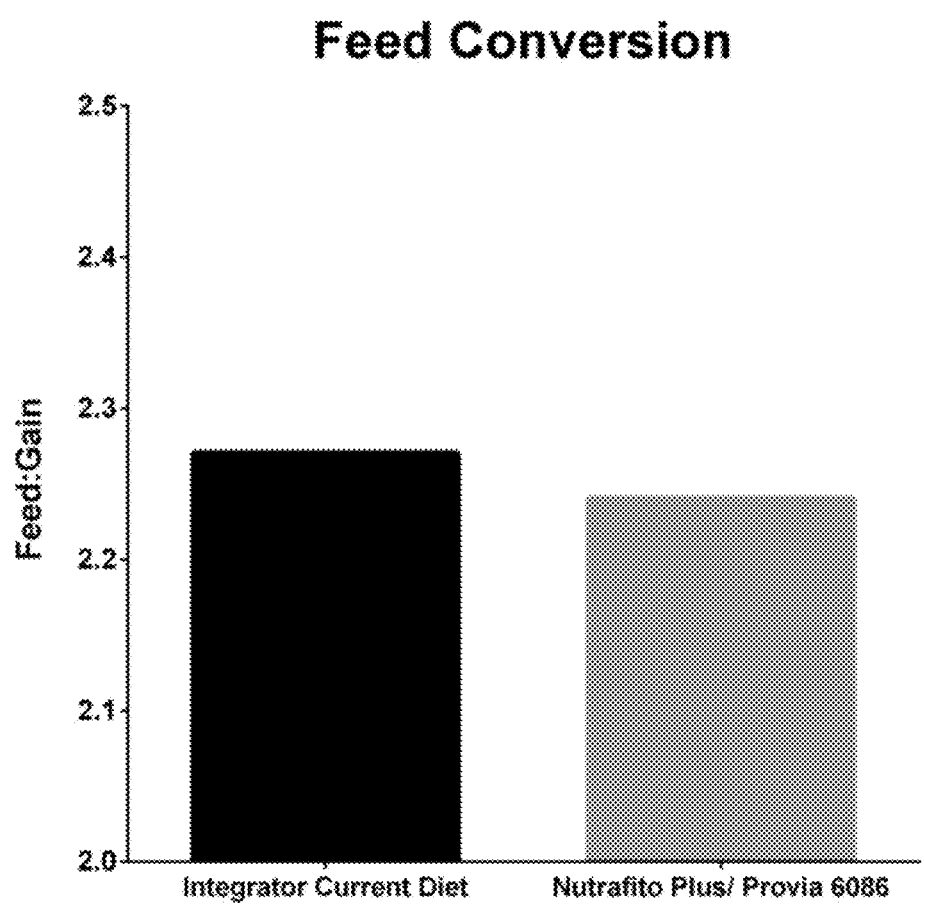
FIG. 62 is a graph of feed conversion ratio versus treatment, illustrating the effect of the combination on the feed conversion ratio of turkeys.

As can be seen in Table 3 and FIGS. 60-62, turkeys fed the supplemented diet had an improved feed conversion ratio, and a lower live weight cost per pound. Table 4 demonstrated the benefits of the combination when the results from Table 3 are extrapolated to a projected annual turnover of over 5 million birds. The improved feed conversion ratio and subsequent lower cost per pound is projected to result in a saving of over two million dollars.

TABLE 4

|  | Group | |
| --- | --- | --- |
|  | Integrator Current Diet | Nutrafito Plus ®/ Provia 6086 ® |
| FY15 Head | 5,575,000 | 5,575,000 |
| Pounds | 256,728,750 | 259,404,750 |
| Weight | 46.05 | 46.53 |
| ADG | 0.3289 | 0.3324 |
| Feed Conversion | 2.27 | 2.24 |
| Feed Cost/Ton | $333 | $332 |
| Live Cost Per LB | $0.5510 | $0.5427 |
| Live Cost Savings | — | $2,142,515 |
| Plant Cost Savings | — | $261,498 |

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A combination for administration to an avian, comprising
a first composition comprising *Quillaja saponaria* plant material and *Yucca schidigera* plant material; and
a second composition comprising *Bacillus coagulans*;
wherein the first composition and the second composition are present in the combination in a ratio of from 2 to 6 ounces of the first composition to from 7 to 8 grams of the second composition.

2. The combination of claim 1, wherein the first composition and the second composition are admixed with an avian feedstuff to form a feedstuff admixture.

3. A composition for administration to an avian, comprising *Quillaja saponaria* plant material, *Yucca schidigera* plant material and *Bacillus coagulans*;
wherein the composition comprises the *Quillaja saponaria* plant material, the *Yucca schidigera* plant material and the *Bacillus coagulans* in a ratio of from 2 to 6 ounces in total of the *Quillaja saponaria* plant material and the *Yucca schidigera* plant material to from 7 to 8 grams of the *Bacillus coagulans*.

4. The composition of claim 3, wherein the composition further comprises a feedstuff.

5. The composition of claim 3, further comprising polyvinylpyrrolidone, tocopheryl polyethylene glycol 1000 succinate, pregelatinized starch, carboxymethylcellulose, or a combination thereof.

6. The composition of claim 4, wherein the composition comprises from 2 to 6 ounces of *Quillaja saponaria* plant material and *Yucca schidigera* plant material per ton of feedstuff and from 7 to 8 grams of *Bacillus coagulans* per ton of feedstuff.

7. A composition for lowering a feed conversion rate of an avian, the composition comprising:
an avian feedstuff comprising polyvinylpyrrolidone, tocopheryl polyethylene glycol 1000 succinate, pregelatinized starch, carboxymethylcellulose, or a combination thereof;
from 2 to 6 ounces *Quillaja saponaria* plant material and *Yucca schidigera* plant material per ton of feedstuff; and
from 7 to 8 grams of *Bacillus coagulans* per ton of feedstuff;
wherein the composition is formulated to lower the feed conversion rate of the avian that is administrated the composition by an amount of from greater than zero to at least 5%, compared to a feed conversion rate of an avian that is not fed the composition.

8. The composition of claim 7, wherein the avian is a chicken.

9. A method for lowering a feed conversion rate in an avian, comprising administering to the avian the combination of claim 1.

10. The method of claim 9, wherein the feed conversion rate is lowered by an amount of from greater than 0 to at least 5%, compared to an avian that is not administered the combination.

11. The method of claim 9, comprising:
providing the first composition comprising *Yucca schidigera* plant material and *Quillaja saponaria* plant material;
providing the second composition comprising *Bacillus coagulans*;
combining the first and second compositions to form a third composition; and
administering the third composition to the avian.

12. The method of claim 11, further comprising mixing the third composition with a feedstuff.

13. The method of claim 9, further comprising combining the combination of *Yucca schidigera* plant material, *Quillaja saponaria* plant material and *Bacillus coagulans* with a feedstuff.

14. The method of claim 9, comprising:
providing the first composition comprising *Yucca schidigera* plant material and *Quillaja saponaria* plant material;
providing the second composition comprising *Bacillus coagulans*;
providing a feedstuff; and
combining the first composition, the second composition and the feedstuff.

* * * * *